US008637042B2

(12) United States Patent
Weiner et al.

(10) Patent No.: US 8,637,042 B2
(45) Date of Patent: *Jan. 28, 2014

(54) TARGETED PARTICLES AND METHODS OF USING THE SAME

(75) Inventors: David B Weiner, Merion, PA (US); Karuppiah Muthumani, Cherry Hill, NJ (US); Donghui Zhang, Philadelphia, PA (US); Mathura Ramanathan, Ardmore, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/422,864

(22) Filed: Mar. 16, 2012

(65) Prior Publication Data
US 2012/0230945 A1 Sep. 13, 2012

Related U.S. Application Data

(62) Division of application No. 10/478,896, filed as application No. PCT/US02/16681 on May 28, 2002, now Pat. No. 8,216,585.

(60) Provisional application No. 60/293,683, filed on May 25, 2001.

(51) Int. Cl.
*A61K 39/21* (2006.01)
*A61K 39/385* (2006.01)
*A61K 39/00* (2006.01)
*C12P 21/04* (2006.01)
*C12N 5/10* (2006.01)

(52) U.S. Cl.
USPC ................ 424/188.1; 424/192.1; 424/195.11; 435/69.7

(58) Field of Classification Search
None
See application file for complete search history.

(56) References Cited

U.S. PATENT DOCUMENTS

| | | |
|---|---|---|
| 4,736,866 A | 4/1988 | Leder et al. |
| 5,017,487 A | 5/1991 | Stunnenberg et al. |
| 5,077,044 A | 12/1991 | Stocker |
| 5,223,424 A | 6/1993 | Cochran et al. |
| 5,225,336 A | 7/1993 | Paoletti |
| 5,240,703 A | 8/1993 | Cochran |
| 5,294,441 A | 3/1994 | Curtiss, III |
| 5,294,548 A | 3/1994 | McLinden et al. |
| 5,310,668 A | 5/1994 | Ellis et al. |
| 5,387,744 A | 2/1995 | Curtiss, III et al. |
| 5,424,065 A | 6/1995 | Curtiss, III et al. |
| 5,451,499 A | 9/1995 | Cochran |
| 5,453,364 A | 9/1995 | Paoletti |
| 5,462,734 A | 10/1995 | Letchworth, III et al. |
| 5,482,713 A | 1/1996 | Paoletti |
| 5,587,308 A | 12/1996 | Carter et al. |
| 5,589,466 A | 12/1996 | Felgner et al. |
| 5,622,856 A | 4/1997 | Natsoulis |
| 5,650,309 A | 7/1997 | Wong-Staal et al. |
| 5,676,594 A | 10/1997 | Joosten |
| 5,703,055 A | 12/1997 | Feigner et al. |
| 5,710,037 A | 1/1998 | Vanin et al. |
| 5,714,316 A | 2/1998 | Weiner et al. |
| 5,716,832 A | 2/1998 | Barber et al. |
| 5,753,500 A | 5/1998 | Shenk et al. |
| 5,817,637 A | 10/1998 | Weiner et al. |
| 5,827,703 A | 10/1998 | Debs et al. |
| 5,830,430 A | 11/1998 | Unger et al. |
| 5,830,876 A | 11/1998 | Weiner et al. |
| 5,834,256 A | 11/1998 | Finer et al. |
| 5,866,411 A | 2/1999 | Pedersen et al. |
| 5,872,005 A | 2/1999 | Wang et al. |
| 5,885,613 A | 3/1999 | Holland et al. |
| 5,888,767 A | 3/1999 | Dropulic et al. |
| 5,891,468 A | 4/1999 | Martin et al. |
| 5,912,338 A | 6/1999 | Rovinski et al. |
| 5,928,913 A | 7/1999 | Efstathiou et al. |
| 5,932,241 A | 8/1999 | Gorman |
| 5,932,467 A | 8/1999 | Khan et al. |
| 5,935,569 A | 8/1999 | Mackiewicz et al. |
| 5,935,936 A | 8/1999 | Fasbender et al. |
| 5,939,401 A | 8/1999 | Marshall et al. |
| 5,945,400 A | 8/1999 | Scherman et al. |
| 6,001,985 A | 12/1999 | Kappes et al. |
| 6,043,081 A | 3/2000 | Cohen et al. |
| 6,107,034 A | 8/2000 | Wiegel |
| 6,190,655 B1 | 2/2001 | Lyman et al. |
| 6,365,150 B1 | 4/2002 | Leboulch et al. |
| 6,391,632 B1 | 5/2002 | Dubensky et al. |
| 6,451,593 B1 | 9/2002 | Wittig et al. |
| 6,562,347 B1 | 5/2003 | Kwak et al. |
| 6,660,257 B1 | 12/2003 | McWherter et al. |
| 2002/0015707 A1 | 2/2002 | Rutter et al. |

FOREIGN PATENT DOCUMENTS

| | | |
|---|---|---|
| WO | 90/11092 | 10/1990 |
| WO | 93/17706 | 9/1993 |
| WO | 94/16737 | 8/1994 |
| WO | 94/19456 | 9/1994 |
| WO | 99/09412 | 2/1999 |
| WO | 99/19359 | 4/1999 |
| WO | 01/24764 | 4/2001 |

OTHER PUBLICATIONS

Lee et al., "Isolation and characterization of a mouse interleukin cDNA clone that expresses B-cell stimulatory factor 1 activities and T-cell-and mast-cell-stimulating activities," Proc. Natl. Acad. Set. (1986) 83:2061-2063.
Lee et al., "Regulation of IL-4 gene expression by distal regulatory elements and GATA-3 at the chromatin level," Immunity (2001) 14(4):447-459.
Lennon et al., The I.M.A.G.E. Consortium: an integrated molecular analysis of genomes and their expression/Genomics (1996) 33(1):151-152.

(Continued)

*Primary Examiner* — Doug Schultz
(74) *Attorney, Agent, or Firm* — Pepper Hamilton LLP

(57) ABSTRACT

Drug delivery compositions and methods of delivering compounds are disclosed. Vaccines and methods of immunizing individuals are disclosed. Compositions for drug delivery including gene therapy and methods of treating individuals using such compositions are disclosed.

10 Claims, 1 Drawing Sheet

(56) References Cited

OTHER PUBLICATIONS

Liu et al., Polymorphism in RANTES chemokine promoter affects HIV-1 disease progression/PAMS (1999) 96 (8):4581-4585.
Loetscher et al., "Molecular cloning and expression of the human 55 kd tumor necrosis factor receptor," Cell (1990) 61:351-359.
Macaubas et al., "Regulation of cytokine production in T-cell responses to inhalant allergen:GATA-3 expression distinguishes between Th1- and Th2-polarized immunity," Int. Arch. Allergy Immunol. (2001) 124(1-3):176-179.
MacFarlane et al., /. Biol. Chem. (1997) in press, Accession No. AF020501.
Maeda et al., Cloning of interleukin 2 mRNAs from human tonsils/ Biochem. Biophys. Res. Comm. (1983) 115:1040-1047.
March et al., "Cloning, sequence and expression of two distinct human interleukin-1 complementary DNAs," Nature (1985) 315:641-647.
Marsters et al., "Apo-3, a new member of the rumor necrosis factor receptor family, contains a death domain and activates apoptosis and NF-kappa B," Curr. Biol. (1996) 6:12):1669-1676.
Merr1Field "Solid phase peplide synthesis. I. The synthesis of a tetrapeptide," J.Am. Chem. Soc. (1963) 15:2149-2154.
Minty et al., "Molecular cloning of the MCP-3 chemokine gene and regulation of its expression," Eur. Cytokine Netw., (1993) 4(2):99-110.
Muzio et al., "FLICE, a novel FADD-homologous ICE/CED-3-like protease, is recruited to the CD95 (Fas/APO-1) death-inducing signaling complex," Cell (1996) 85(6):817-827.
Neote et al., "Molecular cloning, functional expression, and signaling characteristics of a C-C chemokine receptor," Cell (1993) 72(3):415-425.
Noma et al., "Cloning of cDNA encoding the murine IgGI induction factor by a novel strategy using SP6 promoter," Nature (1984) 319:640-646.
Nomura et al., "Molecular cloning of cDNAs encoding a LD78 receptor and putative leukocyte chemotactic peptide receptors," Int. Immunol.__{1993) 5(10):1239-1249.
Nophar et al., "Soluble forms of tumor necrosis factor receptors (TNF-Rs). The cDtiA for the type ITNF-R, cloned using amino acid sequence data of its soluble form, encodes both the cell surface and a soluble form of the receptor," EMBO J. (1990) 9(10):3269-3278.
Oehm et al., "Purification and molecular cloning of the APO-1 cell surface antigen, a member of .the tumor necrosis factor/nerve growth factor receptor superfamily. Sequence identity with the Fas antigen,"/. Biol. Chem. (1992) 267 (15):10709-10715.
Oksenberg et al., "Limited heterogeneity of rearranged T-cell receptor V alpha transcripts in brains of multiple sclerosis patients," Nature (1990) 345:344-346.
Otsuka et al., "Structural analysis of the mouse chromosomal gene encoding interleukin 4 which expresses B cell, T cell and mast cell stimulating activities," Nucl. Acids Res. (1987) 15:333-344.
Paliard et al., "Evidence for the effects of a superantigen in rheumatoid arthritis," Science (1991) 253:325-329.
Pan et al., "The receptor for the cytotoxic ligand TRAIL," Science (1997) 279(5309):III-113.
Paolella et al., Nuclease resistant ribozymes with high catalytic activity/EMBO (1992) 1913-1919.
Pennica "Human tumour necrosis factor: precursor structure, expression and homology to lymphotoxin," Nature (1984) 312:724-729.
Ranganath et al., "Structure and specificity of GATA proteins in Th2 development," Mol. Cell. Biol. (2001) 21(8):2716-2725.
Raport et al., "Molecular cloning and functional characterization of a novel human CC chemokine receptor (CCR5) for RANTES, MIP-Ibeta, and MIP-Ialpha," /. Biol. Chem< (1996) 271(29):17161-17166.
Reeves et al., "The costimulatory genes Cd80 and Cd86 are linked on mouse chromosome 16 and human chromosome 3," Mamm. Geome (1997) 8(8):581-582.
Sakaguchi "Regulatory T cells: key controllers of immunologic self-tolerance," Cell (2000) 101:455-58.

Sato et al., "FAP-1: a protein tyrosine phosphatase that associates with Fas," Science (1995) 268(5209)411-415.
Screaton et al., "LARD: a new lymphoid-specific death domain containing receptor regulated by alternative pre-mRNA splicing," Proc. Natl. Acad. Sri. (1997) 94(9) 4615-4619.
Selvakumar et al., "Genomic organization and chromosomal location of the human gene encoding the B-lymphocyte activation antigen B7," Immunogenetic (1992) 36(3):175-181.
Sheridan et al., "Control of TRAIL-induced apoptosis by a family of signaling and decoy receptors," Science (1997) 277(5327):818-821.
Small et al., "STK-1, the human homolog of Flk-2/Flt-3, is selectively expressed in CD34+ human bone marrow cells and is involved in the proliferation of early progenitor/stem cells," Proc. Natl. Acad. Sci. (1994) 91:459463.
Smits et al., "IL-12-induced reversal of human Th2 cells is accompanied by full restoration of IL-12 responsiveness and loss of GATA-3 expression," Eur. J. Immunol. (2001) 31(4)1055-1065.
Aruffo et al., "The CD40 ligand, gp39, is defective in activated t cells from patients with x-linked hyper-IgM syndrome," Cell (1993) 72:291-300.
Staal et al., "Transcriptional control of t lymphocyte differentiation," Stem Cells (2001) 19(3):165-179.
Stamenkovic et al., "A B-lymphocyte activation molecule related to the nerve growth factor receptor and induced by cytokines in carcinomas," Embo. J. (1989) 8(5):1403-1410.
Stanger et al., "RIP: a novel protein containing a death domain that interacts with Fas/APO-1 (CD95) in yeast and causes cell death," Cell (1995) 81(4):513-523.
Szabo et al., "A novel transcription factor, T-bet, directs Th1 lineage commitment," Cell (2000) 100:655.
Tanabe et al., "Molecular cloning and structure of the human interleukin-5 gene," /. Biol. Chem. (1987) 262:16580-16584.
Taniguchi et al., "Structure and expression of a cloned cDNA for human interleukin-2," Nature (1983)302:305-310.
Telford et al., "The murine interleukin 1 beta gene: structure and evolution," Nucl. Adds. Res. (1986) 14:9955-9963.
Tilbrook et al., "Maturation of erythroid cells and erythroleukemia development are affected by the kinase activity of Lyn," Lyn. Cancer Res. (2001) 61 (6):2453-2458.
Tingvall et al., "The GATA factor Serpent is required for the onset of the humoral immune response in *Drosophila* embryos," Proc. Natl. Acad. Sci. (2001) 98(7):3884-3888.
Toor et al., "T-cell factor-1 expression during human natural killer cell development and in circulating CD56(+) bright natural killer cells," Exp. Hematol. (2001) 29(4):499-506.
Tremblay et al., "Nuclear receptor Dax-1 represses the transcriptional cooperation between . GATA-4 and SF-1 in Sertoli cells," Biol. Reprod. (2001) 64(4):1191-1199.
Ushio et al., "Cloning of the cDNA for human IFN-gamma-inducing factor, expression in *Escherichia coli*, and studies on the biologic activities of the protein," /. Immunol. (1996) 156:4274-4279.
Vieira et al., "Isolation and expression of human cytokine synthesis inhibitory factor cDNA clones: Homology to Epstein-Barr virus open reading frame BCRFI," Proc. Natl. Acad. Sci. (1991) 88:1172-1176.
Visvader et al., Differential transcription of exon 1 of the human c-fms gene in placental trophoblasts and monocytes/Mol. Cell. Biol. (1989) 9(3):1336-1341.
Williams et al., "Restricted heterogeneity of T cell receptor transcripts in rheumatoid synovium," /. Clin. Invest. (1992) 90:326-333.
Ahmad et al., "CRADD, a novel human apoptotic adaptor molecule for caspase-2, and FasL/tumor necrosis factor receptor-interacting protein RIP," Cancer Res. (1997) 57(4):615-619.
Alderson et al., "Molecular and biological characterization of human 4-1BB and its ligand," Eur, }. Immunol. (1994) 24(9):2219-2227.
Alderson et al., Fas ligand mediates activation-induced cell death in human T lymphocytes/ /. Exp. Med. (1995) 181(I):71-7.
Arai et al., "Complete nucleotide sequence of the chromosomal gene for human IL-4 and its expression,"/. Immunol. (1989) 142:274-282.
Azuma et al., "B70 antigen is a second ligand for CTLA-4 and CD28,"Nafure (1993) 366(6450)76-79.
Azuma et al., Cloning of cDNA for human T-cell replacing factor (interleukin-5) and comparison with the murine homologue/Nud. Acids. Res. (1986) 14:9149-9158.

(56) References Cited

OTHER PUBLICATIONS

Behr et al., "Efficient gene transfer into mammalian primary endocrine cells with lipopolyamine-coated DNA,"Proc Nail. Acad. Set. (1989) 86:6982-6986.
Bodmer et al., "TRAMP, a novel apoptosis-mediating receptor with sequence homology to tumor necrosis factor receptor 1 and Fas(Apo-I/CD95),"7mmumry (1997) 6(I):79-88.
Boldin et al., "A novel protein that interacts with the death domain of Fas/APOl contains a sequence motif related to the death domain,"/. Biot. Chem. (1995) 270(14):7795-7798.
Bonnert et al., "The cloning and characterization of human MyD88: a member of an IL-1 receptor related family,"F £BS Lett. (1997) 402(I):81-84.
Campbell et al., "Molecular cloning, nucleotide sequence, and expression of the gene encoding human eosinophil differentiation factor (interleukin 5),"Proc. Natl. Acad. Sci. (1987) 84:6629-6633.
Campbell et al., "Isolation, structure and expression of cDNA and genomic clones for murine eosinophil differentiation factor. Comparison with other eosinophilopoietic lymphokines and identity with interleukin-5," Eur. ]. Biochem. (1988) 174:345-352.
Cerretti et al., "Human macrophage-colony stimulating factor: alternative RNA and protein processing from a single gene,"Mo/. Immunol. (1988) 25(8):761-770.
Charo et al., Molecular cloning and functional expression of two monocyte chemoattractant protein 1 receptors reveals alternative splicing of the carboxyl-terminal tails/ PAMS (1994) 91(7):2752-2756.
Chaudhary et al., A rapid method of cloning functional variable-region antibody genes in *Escherichia coli* as single-chain immunotoxins/Proc. Natl. Acad. Sci. (1990) 87:1066.
Chinnaiyan et al., Signal transduction by DR3, a death domain-containing receptor related to TNFR-1 and CD95, Science. 19% Nov. 8;274(5289):990-2.
Christodoulopoulos et al., "TH2 cytokine-associated transcription factors in atopic and nonatopic asthma: evidence for differential signal transducer and activator of transcription 6 expression,"/. Allergy Clin. Immunol. (2001) 107(4):586-591.
Comb Adiere et al., "Cloning and functional expression of a human eosinophil CC chemokine receptor,"/. Biol. Chem. (1995) 270(28):16491-16494.
Combadiere et al., "Cloning and functional expression of a human eosinophil CC chemokine receptor," /. Biol. Chem. (1995) 270:30235.
Costa et al., Transcription factors in mouse lung development and function, Am\]. Physiol Lung Cell Mol Physiol. (2001) 280(5):L827-L838.
Crispino et al., "Proper coronary vascular development and heart morphogenesis depend on interaction of GATA-4 with FOG cofactors,"Genes Dev. (2001) 15(7):839-844.
Das et al., A critical role for NF-kappa B in GAT A3 expression and TH2 differentiation in allergic airway inflammation/Nat. Immunol. (2001) 2(I):45-50.
Devos et al., Molecular cloning of human interleukin 2 cDNA and its expression in *E. coli*/Nurf. Acids. Res. (1983) 11:4307-4323.
Daugherty et al, "Cloning, expression, and characterization of the human eosinophil eotaxin receptor,"/. Exp. Med. (1996) 183(5):2349-2354.
Duan et al., "Role of NF-Y in in vivo regulation of the gamma-globin gene," Mol. Cell Biol. (2001) 21(9):3083-3095.
Edgington "Ribozymes: stop making sense," Biotechnology (1992) 10:256-262.
Freeman et al, "The gene for B7, a costimulatory signal for T-cell activation, maps to chromosomal region 3ql3.3-3q21," Blood (1992) 79(2):489-494.
Fujita et al, "Structure of the human interleukin 2 gene," Proc. Natl. Acad. Set. (1983) 80:7437-7441.
Furutani et al., "Complete nucleotide sequence of the gene for human interleukin 1 alpha," Nucl. Acids Res. (1986) 14:3167-3179.
Fuse et al, "Organization and structure of the mouse interleukin-2 gene," Nucl. Acids. Res. (1984) 12:9323-9331.

Gao et al., "Structure and functional expression of the human macrophage inflammatory protein 1 alpha/RANTES receptor," /. Exp. Med. (1993) 177(5):1421-1427.
Gauchat et al., "Human CD40-ligand: molecular cloning, cellular distribution and regulation of expression by factors controlling IgE production," Febs. Lett. (1993) 315(3):259-266.
Gilleard et al., "Activation of hypodermal differentiation in the *Caenorhabditis elegans* embryo by GATA transcription factors ELT-1 and ELT-3,"CeW Biol. (2001) 21(7):2533-2544.
Grabstein et al., "Cloning of a T cell growth factor that interacts with the beta chain of the interleukin-2 receptor," Science (1994) 264:965-968.
Graf et al., "Cloning of TRAP, a ligand for CD40 on human T cells," Eur. ]. Immunol. (1992) 22(12):3191-3194.
Gray Cloning and expression of cDNA for human lymphotoxin, a lymphokine with tumour necrosis activity/Natwre (1984) 312:721-724.
Grogan et al., "Early transcription and silencing of cytokine genes underlie polarization of T helper cell subsets," Immunity (2001) 14(3):205-215.
Holbrook et al., "T-cell growth factor: complete nucleotide sequence and organization of the gene in normal and malignant cells," Proc. Natl. Acad. Set. (1984) 81:1634-1638.
Hollenbaugh et al., "The human T cell antigen gp39, a member of the TNF gene family, is a ligand for the CD40 receptor: expression of a soluble form of gp39 with B cell co-stimulatory activity," Embo. /. (1992) 11(12):4313-4321.
Howell et al., ",Limited T-cell receptor beta-chain heterogeneity among interleukin 2 receptor-positive synovial T cells suggests a role for superantigen in rheumatoid arthritis," Proc. Natl. Acad. Set. (1991) 88:10921-10925.
Hsu et al., "The TNF receptor 1-associated protein TRADD signals cell death and NF-kappa 5 activation," Cell (1995) 81(4):495-504.
Itoh et al., The polypeptide encoded by the cDNA for human cell surface antigen Fas can mediate apoptosis/Cell (1991) 66(2):233-243.
Johnson et al., Expression and structure of the human NGF receptor/ Cell (1986) 47(4):545-554.
Kawasaki et al., Molecular cloning of a complementary DNA encoding human macrophage-specific colony-stimulating factor (CSF-1) Science (1985) 230(4723):29-57.
Kent et al., "Modern methods for the chemical synthesis of biologically active peptides," Synthetic Peptides in Biology and Medicine (1996) pp. 295-358.
Kitajima et al., "A role of jumonji gene in proliferation but not differentiation of megakaryocyte lineage cells," Exp. Hematol. (2001) 29(4):507-514.
Kltson et al., "A death-domain-containing receptor that mediates apoptosis," Nature (1996) 384(6607):372-5.
Kuhmann et al., "Polymorphisms in the CCR5 genes of African green monkeys and mice implicate specific amino acids in infections by simian and human immunodeficiency viruses," /. Virol. (1997)71(II):8642-8656.
Lantelme "Kinetics of GATA-3 gene expression in early polarizing and committed human T cells," Immunology (2001) 102(2):123-130.
Lee et al., "The genomic organization of the CD28 gene. Implications for the regulation of CD28 mRNA expression and heterogeneity," /. Immunol (1990) 145(I):344-352.
Wong et al., "Human CSF-1: molecular cloning and expression of 4-kb cDNA encoding the human urinary protein,"Science (1987) 235(4795):1504-1508.
Wong et al., "Organization and differential expression of the human monocyte chemoattractant protein 1 receptor gene. Evidence for the role of the carboxyl-terminal tail in receptor trafficking," /. Bid. Chem. (1997) 272(2):1038-1045.
Wong et al., "Regulation of human monoamine oxidase B gene by Spl and Sp3," Mol. Pharmacol. (2001) 59(4):852-859.
Wright et al., "In vivo regulation of the beta-myosin heavy chain gene in hypertensive rodent heart," Am. J. Physiol. Cell Physiol. (2001) 280(5):C1262-C1276.
Wucherpfenning et al., "Shared human T cell receptor V beta usage to immunodominant regions of myelin basic protein," Science (1990) 248:1016-1019.

(56) References Cited

OTHER PUBLICATIONS

Yamagami et al., "cDNA cloning and functional expression of a human monocyte chemoattractant protein 1 receptor," Biochem. Biophys. Res. Commun. (1994) 202(2):1156-1162.

Yokota et al., "Isolation and characterization of a human interleukin cDNA clone, homologous to mouse B-cell stimulatory factor 1, that expresses B-cell- and T-cell-stimulating activities," Proc. Natl. Acad. Sci. (1986) 83:5894-5898.

Yokota et al., "Isolation and characterization of lymphokine cDNA clones encoding mouse and human IgA-enhancing factor and eosinophil colony-stimulating factor activities: Relationship to interleukin 5," Proc. Natl. Acad. Sci. (1986) 84:7388-7392.

Wu, et al., "Molecular cloning and functional analysis of the mouse homologue of the KILLER/DR5 tumor necrosis factor-related apoptosis-inducing ligand (TRAIL) death receptor," Cancer Research (1999)59:2770-2775.

Hung, et al., Enhancement of DNA vaccine potency by linkage of antigen gene to a gene encoding the extracellular domain of Fms-like tyrosine kinase 3-ligand, Cancer Res. Feb. 1, 2001;61(3):1080-8.

Brand, et al., Antigenic properties of recombinant envelope glycoproteins derived from T-cell-line-adapted isolates or primary human immunodeficiency virus isolates and their relationship to immunogenicity, Virology. Jun. 5, 2000;271 (2):350-62.

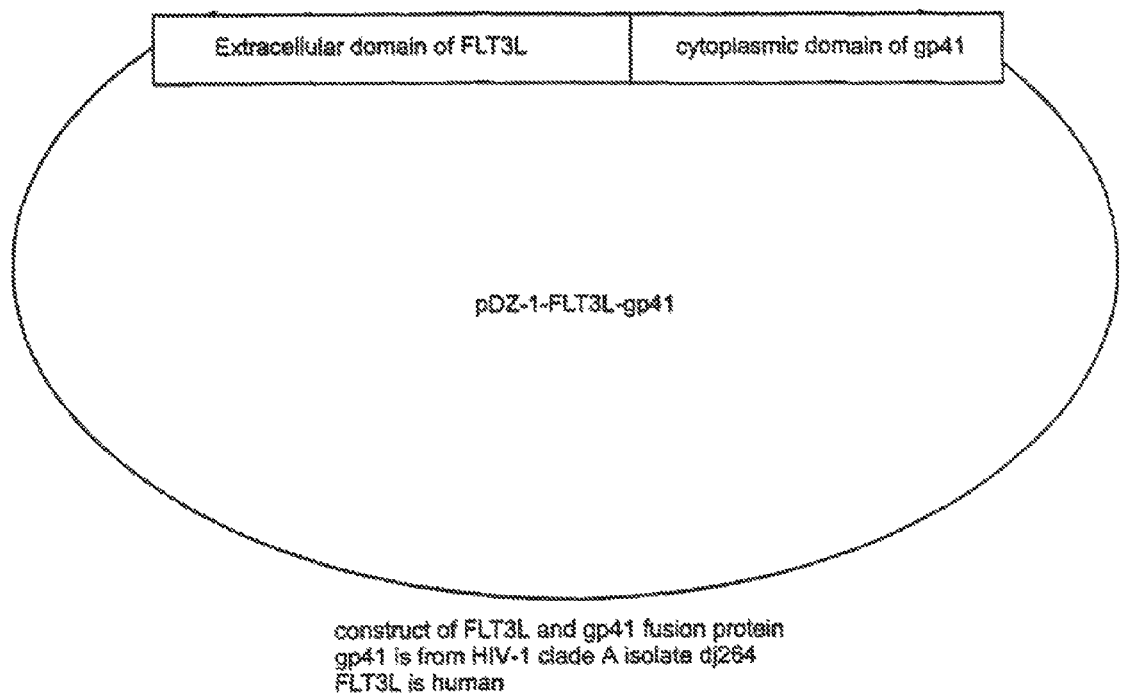

TARGETED PARTICLES AND METHODS OF USING THE SAME

CROSS-REFERENCE TO RELATED APPLICATIONS

This application is a divisional of U.S. patent application Ser. No. 10/478,896, filed on Aug. 30, 2004 now U.S. Pat. No. 8,216,585, which claims priority to and is a national stage application under 35 U.S.C. §371 of PCT International Application Serial Number PCT/US2002/016681, filed May 28, 2002, which claims priority to U.S. Provisional Patent Application Ser. No. 60/293,683, filed May 25, 2001, each of which is incorporated herein by reference in its entirety.

FIELD OF THE INVENTION

The present invention relates to drug delivery compositions, to methods of delivering compounds to specific cell types, to vaccines, to methods of immunizing individuals, to compositions for drug delivery including gene therapy and to methods of treating individuals using such compositions.

BACKGROUND OF THE INVENTION

U.S. Pat. No. 5,714,316, which is incorporated herein by reference, describes the design and production of viral particles which display heterologous protein sequences on the viral particle envelope.

U.S. Pat. Nos. 4,873,089, 5,227,470 and 5,258,499, which are incorporated herein by reference, describe methods of preparing liposomes that contain proteins displayed on their surfaces in order to target the liposomes to a cell with a cellular protein on its surface that specifically binds to the protein on the surface of the liposome.

U.S. Pat. Nos. 5,837,533, 5,459,127 and Behr, J. P., et al. (1989) Proc. Natl. Acad. Sci. USA 86:6982-6986, which are each incorporated herein by reference, describe the design and production of receptor targeted cationic amphiphile/DNA complexes in which positively charged lipophilic compounds are provided with receptor ligands. The cationic amphiphilic compounds contain receptor ligand moieties which are displayed on the surface of complexes formed when the cationic amphiphile is mixed with DNA. Such teachings may also be applied to cationic lipid/DNA complexes such as those described in U.S. Pat. Nos. 5,955,365, 5,948,767, 5,945,400, 5,939,401, 5,935,936, 5,932,241, 5,925,628, 5,916,803, 5,910,488, 5,908,635, 5,891,468, 5,885,613, 5,830,430, 5,827,703, 5,783,565 and 5,767,099, which are incorporated herein by reference.

Improved particles for the delivery of compounds is described in Ser. No. 09/680,690 and PCT/US00/27618, which are incorporated herein by reference. The subject matter described therein includes the use of providing particles that comprise co-stimulatory molecule ligands in order to target cells that express the co-stimulatory molecules. The particles that comprise the co-stimulatory molecule ligands bind to and are taken up by cells that express the co-stimulatory molecules. Thus, compounds that are components of the particle are taken up by the cells.

The use of fusion proteins that comprise a portion of the HIV Vpr protein linked to biologically active non-HIV proteins is described in Ser. No. 08/167,608 filed Dec. 15, 1993 and PCT/US94/02191 filed Feb. 22, 1994, which are incorporated herein by reference. The subject matter described therein sets forth the use of such fusion proteins to deliver biologically active proteins using HIV particles, preferably non-replicating HIV particles to deliver the fusion proteins. About 2400 copies of the Vpr protein are packaged within the HIV particle. By providing fusion proteins with Vpr sequences that interact with the HIV particle, 2400 copies of the fusion protein can be packaged within an HIV-derived particle. Packaging systems are described in each of the following U.S. patents which are incorporated herein by reference: U.S. Pat. Nos. 5,932,467, 5,952,225, 5,932,467, 5,928,913, 5,919,676, 5,912,338, 5,888,767, 5,872,005, 5,866,411, 5,843,723, 5,834,256, 5,753,500, 5,739,018, 5,736,387, 5,723,287, 5,716,832, 5,710,037, 5,693,531, 5,672,510, 5,665,577, 5,622,856, 5,587,308 and 5,585,254.

The delivery of heterologous gene sequences for expression includes those delivered using particles as well as those which are free of such particles. For example, nucleic acid sequences may be included in viral-derived particles, liposomes or other complexes as well as in the form of free DNA delivered with or without co-agents. There are many well known applications, such as vaccine and gene therapy, for delivering nucleic acid molecules in expressible constructs to be taken up by cells and expressed. DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference.

There remains a need for improved particles for delivery of compounds to cells. There remains a need for improved expression systems for nucleic acid molecules delivered to cells.

SUMMARY OF THE INVENTION

The present invention provides three improvements which can be employed independently or in combination in methods of delivering compounds to an individual. One such improvement relates to methods of and compositions for particle based delivery of compounds. One such improvement relates to methods of and compositions for particle based delivery of compounds employing viral particles, or particles derived therefrom. One improvement can be applied to any method and composition for delivery of DNA that is to be expressed in cells.

According to some aspects of the present invention, compositions and methods are provided for the delivery of heterologous gene sequences for expression in cells of an individual using gene constructs that include expression sequences from AAV, adenovirus or alpha viruses such as SFV. The expression sequences include the sequences responsible for both integration and expression and the constructs are free of the AAV, adenovirus or alpha viruses particles from which the expression sequences are derived. In some embodiments, the constructs are included in viral-derived particles, liposomes or other complexes as well as in the form of free DNA delivered with or without co-agents. In some embodiments, the constructs include a packaging signal so that the nucleic acid molecule gets incorporated into a viral particle.

According to aspects of the invention, fusion proteins are provided which comprise HIV Vpr sequences and biologically active portions selected from the group consisting of transcription factors, growth factors, cytokines, chemokines, transport proteins and processing proteins. The Vpr derived portion includes sequences which are required for Vpr protein, and therefor the fusion protein, to be packaged within an HIV derived particle. Optionally, the portions are linked by a protease cleavage site.

Some aspects of the present invention arises from the discovery that non cellular particle that comprises the compound and a FLT-3 ligand are particularly useful to deliver a compound into a cell that expresses FLT-3 molecules. Accordingly, one aspect of the invention relates to methods of introducing a compound into cells that expresses FLT-3 molecules. The methods comprise contacting the cell with a non-cellular particle that comprises the compound and a FLT-3 ligand. In some embodiments, the compound is a nucleic acid molecule or protein.

BRIEF DESCRIPTION OF THE FIGURES

FIG. 1 shows a construct used in the invention to produce a fusion protein comprising the extracellular domain of LFT-3 ligand and the cytoplasmic domain of gp41.

DESCRIPTION OF PREFERRED
EMBODIMENTS OF THE INVENTION

Definitions

As used herein, the term "compound" is meant to refer to any molecule including, but not limited to, a nucleic acid molecule such as DNA or RNA, or a proteinaceous molecule such as a peptide, polypeptide or protein.

As used herein, the term "non-cellular particle" is meant to refer to any particulate structure except a cell.

As used herein, the phrase "cell that expresses costimulatory molecules" is meant to refer to any cell that expresses one or more costimulatory molecules. Such cells are generally antigen presenting cells such as macrophage, granulocyte, dendretic, monocyte, or B cells. Examples of costimulatory molecules are CD80, CD86, CD40, ICOSL, ICAM-1, 41BB, M-CSFR, FLT3, CCR-5, CCR-3, and CCR-2.

As used herein, the phrase "costimulatory ligand" is meant to refer to a molecule that specifically binds to a costimulatory molecule. The costimulatory ligand is a preferably protein, more preferably an anti-costimulatory molecule antibody, a natural ligand that is specific for the costimulatory molecule, fragments thereof or a fusion protein which includes a portion which specifically binds to a costimulatory molecule. In some embodiments, the portion of a fusion protein which specifically binds to a costimulatory molecule is an anti-costimulatory molecule antibody, a natural ligand that is specific for the costimulatory molecule, or fragments thereof. The fusion protein may further comprise portions which perform other functions.

As used herein, the term "natural ligand that is specific for the costimulatory molecule" is meant to refer to the cellular protein present on cells which binds to the costimulatory molecule present on another cell. For example, CD28 and CTLA-4 are both natural ligands for CD80, CD28 is also a natural ligand for CD86, the natural ligand for CD40 is CD40L, the natural ligand for ICOSL is ICOS, the natural ligand for ICAM-1 is LFA-3, the natural ligand for 41BB is 41BBL, the natural ligand for MCSFR is MCSF, the natural ligand for FT3 is FL3L, the natural ligand for CCR2, CGR3 and CCR5 are MCP-3, and RANTES.

As used herein, the phrase "Flt-3 ligand" is meant to refer to a molecule that specifically binds to a Flt-3 molecule. The Flt-3 ligand is a preferably protein, more preferably an anti-Flt-3 molecule antibody, the natural ligand that is specific for the Flt-3 molecule, fragments thereof or a fusion protein which includes a portion of the natural ligand that is specific for the Flt-3 molecule which specifically binds to Flt-3. In some embodiments, the portion of a fusion protein which specifically binds to Flt-3 is an anti-Flt-3 antibody, the natural ligand that is specific for Flt-3, or fragments thereof. The fusion protein may further comprise portions which perform other functions.

As used herein, the term "antibody" is meant to refer to antibodies, as well as antibody fragments such as FAb and $F(Ab)_2$ fragments. Antibodies may, in some preferred embodiments, be monoclonal antibodies, primatized antibodies or humanized antibodies. Antibodies may, in some preferred embodiments, be murine or human antibodies.

As used herein, the term "cationic amphipbile/DNA complex" is meant to refer to a complex arising from the mixture of DNA and one or more cationic amphiphiles.

As used herein the term "desired protein" is meant to refer to peptides and protein encoded by gene constructs of the present invention which either act as target proteins for an immune response or as a therapeutic or compensating protein in gene therapy regimens.

As used herein, the term "genetic therapeutic" refers to a pharmaceutical preparation that comprises a genetic construct that comprises a nucleotide sequence that encodes a therapeutic or compensating protein.

As used herein, the term "therapeutic protein" is meant to refer to proteins whose presence confers a therapeutic benefit to the individual.

As used herein, the term "compensating protein" is meant to refer to proteins whose presence compensates for the absence of a fully functioning endogenously produced protein due to an absent, defective, non-functioning or partially functioning endogenous gene.

As used herein, the term "biologically active portion" refers to the portion of a fusion protein derived from a biologically active protein which retains and effects its biologically activity when taken up by a cell.

FLT-3 Ligand

It has been discovered that particles that comprise FLT-3 ligand are particularly useful to target cells and deliver compounds to the cells using such particles. It has been discovered that such particles are useful in the absence of a fusion domain. According to a preferred embodiments, a fusion protein is provided that comprises a FLT-3 ligand portion linked to the transmembrane and cytoplasmic portions of HIV gp41. A construct for preparing a fusion protein according to this aspect of the invention is set forth in FIG. 1. HIV env, derived from HIV CCR5 has been found to be particularly useful. Particles assembled by, for example, packaging cell lines that express the fusion protein comprise the FLT-3 ligand portion successfully bind to and are taken up by cells. In some preferred embodiments that include the fusion protein that comprises a FLT-3 ligand portion linked to the transmembrane and cytoplasmic portions of HIV gp41, the particles assembled by a packaging cell line that express the fusion protein and HIV env, preferably that which is derived from HIV CCR5. The use of fusion proteins that comprise a FLT-3 ligand portion can be included in the particles for the delivery of compounds described in PCT/US00/27618, particularly viral particle that contain protein based stalks such as retroviruses, such as lentiviruses, particularly HIV-1 or HIV-2, and herpesviruses, particularly HSV-1 or HSV-2. In some preferred embodiments that include herpes virus-derived particles, the fusion proteins may comprise the FLT-3 ligand portion linked to herpes virus viral protein gD, gB, gH or gL. Embodiments according to this aspect of the invention include particles in which the co-stimulatory ligand as described in Example 2 is FLT-3 ligand.

Vpr Fusion Proteins

According to some aspects of the invention, fusion proteins are provided which in addition to Vpr sequences comprise biologically active portions selected from the group consisting of transcription factors, growth factors, cytokines, chemokines, transport proteins and processing proteins. In some embodiments, the transcription factor is Tbet. When particles that contain such fusion proteins infect cells, the action of the Tbet results in a shifting of the immune response to a Th1 response. Such particles are useful to improve immune responses induced by vaccines. In some embodiments, the transcription factor is Tgata. When particles that contain such fusion proteins infect cells, the action of the Tgata results in a shifting of the immune response to a Th2 response. Such particles are useful to treat patients with autoimmune diseases. Cytokines and chemokines can drive/modulate immune responses. Human proinflammatory cytokines include IL-1α, TNF-α and TNF-β, Th1 cytokines include IL-2, IL-15, and IL-18, and Th2 cytokines include IL-4, IL-5 and IL-10. GM-CSF is another factor which may be delivered according to the invention. In some embodiments, the cytokine is IL-15. In some embodiments, the chemokine is RANTES. Fusion proteins can transport proteins such as p70 or processing proteins such as Tap.

Fusion proteins preferably do not contain Vpr sequences not related to packaging. In particular, fusion proteins preferably do not contain Vpr sequences that are involved in Vpr's cell cycle arrest/apoptosis inducing activity. Vpr sequences with their respective activities are described in published PCT application PCT/US98/16890 and published PCT application PCT/US98/21432, both of which are incorporated herein by reference. The fusion protein may include a protease cleavage site between the Vpr portion and the biologically active portion. An example of such a cleavage site is the cleavage site recognized by the HIV protease. In addition to HIV-derived particles, the invention is envisioned to include particles and fusion proteins based upon other lentiviruses and lentivirus proteins. The production and use of particles according to this aspect of the invention is described in Examples 2 and 3 below. The invention also pertains to the use of free Vpr fusions to be delivered as drugs as well.

DNA Constructs

According to some aspects of the present invention, compositions and methods are provided for the delivery of heterologous gene sequences for expression in cells of an individual using gene constructs that include expression sequences from AAV, adenovirus or alpha viruses such as SFV. The expression sequences include the sequences responsible for both integration and expression and the constructs are free of the AAV, adenovirus or alpha viruses particles from which the expression sequences are derived. The constructs may be included in viral-derived particles, liposomes or other complexes as well as in the form of free DNA delivered with or without co-agents. The constructs are preferably included in particles that will not cross react to the immune response generated against a potent expression viral vectors. This will allow boosts while taking advantage of the high expression characteristics of the potent expression viral vectors. In preferred embodiments, the constructs are part of retrovirus derived viral particles. The potent expression sequences contain the regulatory sequences, such as the ITR sequences in the case of AAV, a gene of interest and a packaging signal so that the nucleic acid molecule gets incorporated into the viral particle.

Combinations

According to the present invention, compositions include one, two or all three of the above-described improvements. That is, in some embodiments, particles are provided with fusion proteins that include a FLT-3 ligand portion. In some embodiments, particles are provided with fusion proteins that include a FLT-3 ligand portion and a fusion protein that includes a Vpr portion and a biologically active portion selected from the group consisting of transcription factors, growth factors, cytokines, chemokines, transport proteins and processing proteins. In some embodiments, particles are provided with fusion proteins that include a FLT-3 ligand portion, a fusion protein that includes a Vpr portion and a biologically active portion selected from the group consisting of transcription factors, growth factors, cytokines, chemokines, transport proteins and processing proteins, and a nucleic acid molecule that comprises expression sequences from AAV, adenovirus or alpha viruses. In some embodiments, particles are provided fusion proteins that include a Vpr portion and a biologically active portion selected from the group consisting of transcription factors, growth factors, cytokines, chemokines, transport proteins and processing proteins. In some embodiments, particles are provided with fusion proteins that include a Vpr portion and a biologically active portion selected from the group consisting of transcription factors, growth factors, cytokines, chemokines, transport proteins and processing proteins, and a nucleic acid molecule that comprises expression sequences from AAV, adenovirus or alpha viruses. In some embodiments, a nucleic acid molecules are provided that comprises expression sequences from AAV, adenovirus or alpha viruses.

The methods of the present invention are useful in the fields of both human and veterinary medicine. Accordingly, the present invention relates to genetic immunization of mammals, birds and fish. The methods of the present invention can be particularly useful for mammalian species including human, bovine, ovine, porcine, equine, canine and feline species.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLES

Example 1

The following sequences identified by accession number and references are incorporated herein by reference.

| | | |
|---|---|---|
| VPR | AJ404325 | vpr, gag, pol, vif, vpu, env, and nef |
| VPR | AF316862 | vif, vpr (Cameroon isolate) |
| VPR | AF325763 | vif, vpr (South African isolate) | macrophage colony-stimulating factor
Accession No. AAA59572
Cerretti, D. P. et al., Mol. Immunol. 25 (8), 761-770 (1988)
Accession No. AAB51235
Visvader, J. and Verma, I. M., Mol. Cell. Biol. 9 (3) 1336-1341 (1989)
Accession No. P09603
Wong et al., Science 235 (4795) 1504-1508 (1987)
Cerretti et al., Mol. Immunol. 25 (8) 761-770 (1988)
Kawasaki et al, Science 230 (4723) 291-296 (1985)
chemokine (C—C motif) receptor 5
Accession No. 4502639
Raport, C. J. et al., J. Biol. Chem. 271 (29), 17161-17166 (1996)
monocyte chemoattractant protein (MCP-3)
Accession No. CAA50407
Minty, A. et al., Eur. Cytokine Netw. 4 (2), 99-110 (1993)
Accession No. AAC03538
pFLT3
fms-related tyrosine kinase 3
Accession No. 4758396
Small, D. et al., Proc. Natl. Acad. Sci. U.S.A. 91, 459-463 (1994)
Accession No. P36888
Small et al., Proc. Natl. Acad. Sci. U.S.A. 91, 459-463 (1994)
pFLT3LG
fms-related tyrosine kinase 3 ligand
Accession No. 4503751
4-1BB
Accession No. AAA53133
Alderson, M. R. et al., Eur. J. Immunol. 24 (9), 2219-2227 (1994)
4-1BBL
Accession No. P41273
Alderson, M. R. et al., Eur. J. Immunol. 24 (9) 2219-2227 (1994)
RANTES
Accession No. BAA76939
Liu, H. et al., PNAS U.S.A. 96 (8), 4581-4585 (1999)
Accession No. 1065018
CCR1/MIP1R
Accession No. P32246
Neote, K. et al., Cell 72 (3) 415-425 (1993)
Gao, J. L. et al., J. Exp. Med. 177 (5) 1421-1427 (1993)
Nomura, H. et al., Int. Immunol. 5 (10) 1239-1249 (1993)
CCR5
Accession No. P56493
Kubmann, S. E. et al., J. Virol. 71 (11) 8642-8656 (1997)
Murayama, Y. et al.
CCR2
Accession No. P41597
Charo, I. F. et al., PNAS, U.S.A. 91 (7) 2752-2756 (1994)
Yamagami, S. et al., Biochem. Biophys. Res. Commun. 202 (2) 1156-1162 (1994)
Wong, L. M. et al., J. Biol. Chem. 272 (2) 1038-1045 (1997)
CCR3
Accession No. P51677
Combadiere, C. et al., J. Biol. Chem. 270 (28) 16491-16494 (1995)
Combadiere, C. et al., J. Biol. Chem. 270 30235 (1995)
Dougherty, B. L. et al., J. Exp. Med. 183 (5) 2349-2354 (1996)
CD40 ligand
Accession No. P29965
Graf, D. et al., Eur. J. Immunol. 22 (12) 3191-3194 (1992)
Hollenbaugh, D. et al., Embo. J. 11 (12) 4313-4321 (1992)
Spriggs, M. K. et al., Cell 72 291-300 (1993)
Spriggs, M. K. et al., J. Exp. Med. 176 (6) 1543-1550 (1992)
Gauchat et al., Febs. Lett. 315 (3) 259-266 (1993)
CD86
Accession No. 5901920
Azuma et al., Nature 366 (6450) 76-79 (1993)
Reeves et al., Mamm. Genome 8 (8) 581-582 (1997)
CD80
Accession No. 4885123
Selvakumar et al., Immunogenetic 36 (3) 175-181 (1992)
Freeman et al., Blood 79 (2) 489-494 (1992)
CD40
Accession No. 4507581
Stamenkovic et al., Embo. J. 8 (5) 1403-1410 (1989)
LFA-3
Accession No. BAA05922
ICAM1
Accession No. AAB51145
CD28
Accession No. 5453611
Lee et al., J. Immunol. 145 (1) 344-352 (1990)

The nucleotide and amino acid sequences of human IL-1α are well known and set forth in Telford, et al. (1986) Nucl. Acids Res. 14:9955-9963, Furutani, et al. (1985) Nucl. Acids Res. 14:3167-3179, March, et al. (1985) Nature 315:641-647, and accession code Swissprot P01583, which are each incorporated herein by reference.

The nucleotide and amino acid sequences of human IL-2 are well known and set forth in Holbrook, et al. (1984) Proc. Natl. Acad. Sci. USA 81:1634-1638, Fujita, et al. (1983) Proc. Natl. Acad. Sci. USA 80:7437-7441, Fuse, et al. (1984) Nucl. Acids Res. 12:9323-9331, Taniguchi, et al. (1983) Nature 302:305-310, Maeda, et al. (1983) Biochem. Biophys. Res. Comm. 115:1040-1047, Devos, et al. (1983) Nucl. Acids Res. 11:4307-4323, and accession code Swissprot P01585, which are each incorporated herein by reference.

The nucleotide and amino acid sequences of human IL-4 are well known and set forth in Arai, et al. (1989). J. Immunol. 142:274-282, Otsuka, et al. (1987) Nucl. Acids Res. 15:333-344, Yokota, et al. (1986) Proc. Natl. Acad. Sci. USA 83:5894-5898, Noma, et al. (1984) Nature 319:640-646, Lee, et al. (1986) Proc. Natl. Acad. Sci. USA 83:2061-2063, and accession code Swissprot 05112 (the accession code for murine IL-4 is Swissprot 07750), which are each incorporated herein by reference.

The nucleotide and amino acid sequences of human IL-5 are well known and set forth in Campbell, et al. (1987) Proc. Natl. Acad. Sci. USA 84:6629-6633, Tanabe, et al. (1987) J. Biol. Chem. 262:16580-16584, Campbell, et al. (1988) Eur. J. Biochem. 174:345-352, Azuma, et al. (1986) Nucl. Acids Res. 14:9149-9158, Yokota, et al. (1986) Proc. Natl. Acad. Sci. USA 84:7388 7392, and accession code Swissprot PO5113, which are each incorporated herein by reference.

The nucleotide and amino acid sequences of human IL-10 are well known and set forth in Viera, et al. (1991) Proc. Natl. Acad. Sci. USA 88:1172-1176, and accession code Swissprot P22301.

The nucleotide an amino acid sequences of human IL-15 are well known and set forth in Grabstein, et al. (1994) Science 264:965-968, and accession code Swissprot U03099, which are each incorporated herein by reference.

The nucleotide and amino acid sequences of human IL-18 are well known and set forth in Ushio, et al. (1996) J. Immunol. 156:4274-4279, and accession code D49950, which are each incorporated herein by reference.

The nucleotide and amino acid sequences of human TNF-α are well known and set forth in Pennica, (1984) Nature 312:

724-729, and accession code Swissprot P01375, which are each incorporated herein by reference.

The nucleotide and amino acid sequences of human TNF-13 are well known and set forth in Gray, (1984) Nature 312: 721-724, and accession code Swissprot P01374, which are each incorporated herein by reference.

T-Bet.:

Susanne J. Szabo, et al., A Novel Transcription Factor, T-bet, Directs Th1 Lineage Commitment, *Cell* 2000 100: 655.

Shimon Sakaguchi, Regulatory T Cells: Key Controllers of Immunologic Self-Tolerance, Cell 2000 101: 455.

The following provides the information from the Database, which provides information for both protein and gene sequences 1: AF241243 PubMed, Protein, Related Sequences, Taxonomy, OMIM *Homo sapiens* T-cell-specific T-box transcription factor T-bet mRNA, complete cds 2: AF241242 PubMed, Protein, Related Sequences, Taxonomy, OMIM *Mus musculus* T-cell-specific T-box transcription factor T-bet mRNA, complete cds 3: NM_013351 PubMed, Protein, Related Sequences, Taxonomy, OMIM *Homo sapiens* T-box 21 (TBX21), mRNA Tbet AF241243 human—also called T-cell specific T-box transcription factor T-Gata.

Staal F J, et al, Transcriptional control of t lymphocyte differentiation. Stem Cells. 2001; 19(3):165-79.

Lee G R, et al., Regulation of IL-4 gene expression by distal regulatory elements and GATA-3 at the chromatin level. Immunity. 2001 April; 14(4):447-59.

Macaubas C, Holt P G. Regulation of cytokine production in T-cell responses to inhalant allergen:GATA-3 expression distinguishes between Th1- and Th2-polarized immunity. Int Arch Allergy Immunol. 2001 January-March; 124(1-3):176-9.

Kitajima K, et al., A role of jumonji gene in proliferation but not differentiation of megakaryocyte lineage cells. Exp Hematol. 2001 April; 29(4):507-14.

Toor A A, et al., T-cell factor-1 expression during human natural killer cell development and in circulating CD56(+) bright natural killer cells. Exp Hematol. 2001 April; 29(4): 499-506.

Smits H H, et al., IL-12-induced reversal of human Th2 cells is accompanied by full restoration of IL-12 responsiveness and loss of GATA-3 expression. Eur J Immunol. 2001 April; 31(4):1055-65.

Crispino J D, et al., Proper coronary vascular development and heart morphogenesis depend on interaction of GATA-4 with FOG cofactors. Genes Dev. 2001 Apr. 1; 15(7):839-44.

Christodoulopoulos P, et al., TH2 cytokine-associated transcription factors in atopic and nonatopic asthma: evidence for differential signal transducer and activator of transcription 6 expression. J Allergy Clin Immunol. 2001 April; 107(4):586-91.

Costa R H, et al., Transcription factors in mouse lung development and function. Am J Physiol Lung Cell Mol. Physiol. 2001 May; 280(5):L823-38.

Grogan J L, et al., Early transcription and silencing of cytokine genes underlie polarization of T helper cell subsets. Immunity. 2001 March; 14(3):205-15.

Tilbrook P A, et al., Maturation of erythroid cells and erythroleukemia development are affected by the kinase activity of L. Cancer Res. 2001 March 15; 61(6):2453-8.

Duan Z, et al., Role of NF-Y in in vivo regulation of the gamma-globin gene. Mol Cell Biol. 2001 May; 21(9):3083-95.

Wright C E, et al., In vivo regulation of the beta-myosin heavy chain gene in hypertensive rodent heart. Am J Physiol Cell Physiol. 2001 May; 280(5):C1262-76.

Ranganath S, Murphy K M. Structure and specificity of GATA proteins in Th2 development. Mol Cell Biol. 2001 April; 21(8):2716-25.

Tingvall T O, et al., The GATA factor Serpent is required for the onset of the humoral immune response in *Drosophila* embryos. Proc Natl Acad Sci USA. 2001 Mar. 27; 98(7): 3884-8.

Das J, et al., A critical role for NF-kappa B in GATA3 expression and TH2 differentiation in allergic airway inflammation. Nat Immunol. 2001 January; 2(1):45-50.

Lantelme E, Kinetics of GATA-3 gene expression in early polarizing and committed human T cells. Immunology. 2001 February; 102(2):123-30.

Wong W K., et al., Regulation of human monoamine oxidase B gene by Sp1 and Sp3. Mol Pharmacol. 2001 April; 59(4): 852-9.

Gilleard J S, McGhee J D. Activation of hypodermal differentiation in the *Caenorhabditis elegans* embryo by GATA transcription factors ELT-1 and ELT-3. Mol Cell Biol. 2001 April; 21(7):2533-44.

Tremblay J J, Viger R S. Nuclear receptor Dax-1 represses the transcriptional cooperation between GATA-4 and SF-1 in Sertoli cells. Biol Reprod. 2001 April; 64(4):1191-9.

1: AE006819 Protein, Related Sequences, Genome, Taxonomy *Sulfolobus solfataricus* section 178 of 272 of the complete genome 2: AL590734 PubMed, Protein, Taxonomy *Leishmania major* chromosome 13 clone PAC P883 strain Friedlin 3: AR106378 Sequence 10 from U.S. Pat. No. 6,107,034

4: AR106377 Sequence 9 from U.S. Pat. No. 6,107,034

5: AR106376 Sequence 8 from U.S. Pat. No. 6,107,034

6: AR106375 Sequence 7 from U.S. Pat. No. 6,107,034

7: AR106374 Sequence 6 from U.S. Pat. No. 6,107,034

8: AR106373 Sequence 5 from U.S. Pat. No. 6,107,034

9: AR106372 Sequence 4 from U.S. Pat. No. 6,107,034

10: AR106371 Sequence 3 from U.S. Pat. No. 6,107,034

11: AR106370 Sequence 2 from U.S. Pat. No. 6,107,034

12: AR106369 Sequence 1 from U.S. Pat. No. 6,107,034

13: AY024364 Protein, Taxonomy *Rattus norvegicus* GATA-3 mRNA, complete cds

14: NM_008091 PubMed, Protein, Related Sequences, Taxonomy *Mus musculus* GATA-binding protein 3 (Gata3), mRNA 15: NM_002051 PubMed, Protein, Related Sequences, Taxonomy, OMIM *Homo sapiens* GATA-binding protein 3 (GATA3), mRNA 16: BB509565 RIKEN full-length enriched, 10 days lactation, adult female mammary gland *Mus musculus* cDNA clone D730025A17 similar to X55123 Mouse mRNA for GATA-3 transcription factor, mRNA sequence 17: BB508018 RIKEN full-length enriched, 10 days lactation, adult female mammary gland *Mus musculus* cDNA clone D730015M23 similar to X55123 Mouse mRNA for GATA-3 transcription factor, mRNA sequence 18: BB501281 RIKEN full-length enriched, 0 day neonate kidney *Mus musculus* cDNA clone D630034A10 3' similar to X55123 Mouse mRNA for GATA-3 transcription factor, mRNA sequence 19: BB497281 RIKEN full-length enriched, 0 day neonate kidney *Mus musculus* cDNA clone D630008B05 3' similar to X55123 Mouse mRNA for GATA-3 transcription factor, mRNA sequence 20: BB121131 RIKEN full-length enriched, adult male urinary bladder *Mus musculus* cDNA clone 9530080K05 3' similar to X55123 Mouse mRNA for GATA-3 transcription factor, mRNA sequence

| Tgata | XM 010214 | Human--GATA1 |
| Tgata | NM002049 | Human--GATA1 |
| Tgata | NM005257 | Human--GATA6 |

Example 2

The present invention relates to methods of introducing compounds into cells that express costimulatory molecules, and to non-cellular particles useful in such methods. According to the methods of the present invention, cells that express costimulatory molecules are contacted with non-cellular particles that comprise a compound in combination with a costimulatory ligand. The costimulatory ligand component of the particle specifically target the cells that express costimulatory molecules. The particles bind to the cells and are taken up by them, thus delivering the compound into the cell.

According to some aspects of the present invention, methods of immunizing individuals are provided. Such methods comprise the step of administering to tissue of the individual at a site on the individual's body, a non-cellular particle that comprises an immunogenic protein or a nucleic acid molecule that encodes an immunogenic protein. The particle additionally comprises costimulatory ligand. The particles bind to the cells and are taken them, thus delivering the immunogenic protein or a nucleic acid molecule that encodes an immunogenic protein into the cell. An immune response is generated against the immunogenic protein delivered to the cell or against the expression product of a nucleic acid molecule which encodes an immunogenic protein and which is taken up by and expressed in the cell.

The present invention may be used to immunize an individual against all pathogens such as viruses, prokaryote and pathogenic eukaryotic organisms such as unicellular pathogenic organisms and multicellular parasites.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis. The present invention provides a method of treating individuals suffering from hyperproliferative diseases. In such methods, the compound provides a target protein against which an immune response that will be specific for proteins expressed by hyperproliferating cells. While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer. Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from autoimmune diseases and disorders by conferring a broad based protective immune response against targets that are associated with autoimmunity including cell receptors and cells which produce "self"-directed antibodies.

According to some aspects of the present invention, methods of delivering therapeutic compounds to individuals are provided. According to such methods, the compound is a therapeutic compound. In some embodiments, the compound is therapeutic protein or a nucleic acid molecule that encodes a therapeutic protein. The methods comprise the step of administering to tissue of the individual at a site on the individual's body, a non-cellular particle that comprises an therapeutic protein or a nucleic acid molecule that encodes an therapeutic protein. The particle additionally comprises costimulatory ligand. The particles bind to the cells and are taken them, thus delivering the therapeutic protein or a nucleic acid molecule that encodes an therapeutic protein into the cell. The therapeutic protein is thus delivered directly to the cell or is produced in the cell by the of the nucleic acid molecule which encodes it and is taken up in the cell.

Some aspects of the present invention relate to gene therapy; that is, to compositions for and methods of introducing nucleic acid molecules into the cells of an individual exogenous copies of genes which either correspond to defective, missing, non functioning or partially functioning genes in the individual or which encode therapeutic proteins, i.e. proteins whose presence in the individual will eliminate a deficiency in the individual and/or whose presence will provide a therapeutic effect on the individual thereby providing a means of delivering the protein by an alternative means from protein administration.

Compounds

Compounds which can be delivered to cells by the methods of the invention may be any molecule. In some embodiments, the compound is a nucleic acid molecule such as DNA or RNA. In some embodiments, the compound is a proteinaceous molecule such as a peptide, polypeptide or protein.

In some embodiments, the compound is a protein molecule. In some embodiments, the compound is an immunogenic protein. In some embodiments, the compound is a non-immunogenic protein molecule.

Examples of immunogenic proteins includes pathogen antigens, proteinaceous allergans, immunogenic proteins associated with cancer cells, and immunogenic proteins associated with cells involved in autoimmune diseases.

Pathogen antigens may be derived from all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, *listeria* and *shigella*. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins. Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2. Tables 1 and 2 include lists of some of the pathogenic agents and organisms for which genetic vaccines can be prepared to protect an individual from infection by them. In some preferred embodiments, the methods of immunizing an individual against a pathogen are directed against HIV, HTLV or HBV.

As used herein, the term "hyperproliferative-associated protein" is meant to refer to proteins that are associated with a hyperproliferative disease. To immunize against hyperproliferative diseases, a "hyperproliferative-associated protein" or a genetic construct that includes a nucleotide sequence which encodes a protein that is associated with a hyperproliferative disease is included as the compound in the particle administered to an individual. In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins which are found at higher levels in tumor cells including the protein recognized by monoclonal antibody 17-1A and folate binding proteins.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable regions of the T cells would elicit an immune response including CTLs to eliminate those T cells.

In RA, several specific variable regions of T cell receptors (TCRs) which are involved in the disease have been characterized. These TCRs include V$\beta$-3, V$\beta$-14, V$\beta$-17 and V$\alpha$-17. Thus, vaccination with a particle that contains as the compound one of these proteins or a DNA construct that encodes at least one of these proteins will result in the generation of an immune response that will target T cells involved in RA. See: Howell, M. D., et al., 1991 *Proc. Natl. Acad. Sci. USA* 88:10921-10925; Paliard, X., et al., 1991 *Science* 253:325-329; Williams, W. V., et al., 1992 *J. Clin. Invest.* 90:326-333; each of which is incorporated herein by reference.

In MS, several specific variable regions of TCRs which are involved in the disease have been characterized. These TCRs include V$\beta$-7 and V$\alpha$-10. Thus, vaccination with a particle that contains as the compound one of these proteins or a DNA construct that encodes at least one of these proteins will result in the generation of an immune response that will target T cells involved in MS. See: Wucherpfennig, K. W., et al., 1990 *Science* 248:1016-1019; Oksenberg, J. R., et al., 1990 *Nature* 345:344-346; each of which is incorporated herein by reference.

In scleroderma, several specific variable regions of TCRs which are involved in the disease have been characterized. These TCRs include V$\beta$-6, V$\beta$-8, V$\beta$-14 and V$\alpha$-16, V$\alpha$-3C, V$\alpha$-7, V$\alpha$-14, V$\alpha$-15, V$\alpha$-16, V$\alpha$-28 and V$\alpha$-12. Thus, vaccination with a particle that contains as the compound one of these proteins or a DNA construct that encodes at least one of these proteins will result in the generation of an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Particles useful to immunize against the disease can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Particles useful to immunize against such diseases can be prepared using this information.

In the case of SLE, one antigen is believed to be DNA. Thus, in patients to be immunized against SLE, their sera can be screened for anti-DNA antibodies and a vaccine can be prepared which includes the variable region of those antibodies or DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K, et al., 1990 *Proc. Natl. Acad. Sci. USA* 87:1066, which is incorporated herein by reference.

In some embodiments the compound in the particle is a non-immunogenic protein which may serve as replacement protein in individuals suffering from diseases associated with defective, missing or non-functioning genes. The non-immunogenic proteins may alternatively be therapeutic proteins. In some embodiments the compound in the particle is a nucleic acid molecule which serves as: 1) replacement copies of defective, missing or non-functioning genes; 2) genetic templates for therapeutic proteins; 3) genetic templates for antisense molecules; or 4) genetic templates for ribozymes. In the case of nucleic acid molecules which encode proteins, the nucleic acid molecules preferably comprise the necessary regulatory sequences for transcription and translation in the cells of the animal. In the case of nucleic acid molecules which serve as templates for antisense molecules and ribozymes, such nucleic acid molecules are preferably linked to regulatory elements necessary for production of sufficient copies of the antisense and ribozyme molecules encoded thereby respectively. The nucleic acid molecules are free from retroviral particles and preferably provided as DNA in the form of plasmids.

In some of the embodiments of the invention that relate to gene therapy, the gene constructs contain either compensating genes or genes that encode therapeutic proteins. Examples of compensating genes include a gene which encodes dystrophin or a functional fragment, a gene to compensate for the defective gene in patients suffering from cystic fibrosis, an insulin, a gene to compensate for the defective gene in patients suffering from ADA, and a gene encoding Factor VIII. Additionally, genetic constructs which encode antibodies, such as single chain antibody components which specifically bind to toxic substances, can be administered. In some embodiments, antibodies expressed in such cells can be secreted. In some preferred embodiments, the dystrophin gene is provided as part of a mini-gene and used to treat individuals suffering from muscular dystrophy. In some preferred embodiments, a mini gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is chair-bound by age 13 and usually dies by age 20. In some patients, particularly those suffering from BMD, partial dystrophin protein produced by expression of a mini-gene delivered according to the present invention can provide improved muscle function.

Examples of therapeutic proteins include the proteins themselves and the genes which encodes active proteins such as cytokines, growth factors, chemokines as well as toxins. In some embodiments, the protein is erythropoietin, interferon, LDL receptor, GM-CSF, IL-2, IL-4 or TNF. Therapeutic proteins or nucleic acid molecules that encode therapeutic proteins may be included in particles as a compound to be delivered to cells. Therapeutic proteins that are toxins or otherwise toxic or cytostatic to the cell are useful for example when delivered to antigen presenting cells in patients with lymphoproliferative diseases. In addition to toxins, other antiproliferative proteins are antibodies, HIV Vpr and TGFβ. Therapeutic proteins that expand APC numbers include growth factors such as EPO, CSF and GCSF. Proteins which modulate immune responses may be delivered to cells in this manner in order to modulate immune responses in an individual.

Antisense molecules and ribozymes may also be delivered to the cells of an individual by introducing genetic material which acts as a template for copies of such active agents. These agents inactivate or otherwise interfere with the expression of genes that encode proteins whose presence is undesirable. Constructs which contain sequences that encode antisense molecules can be used to inhibit or prevent production of proteins within cells. Thus, production proteins such as oncogene products can be eliminated or reduced. Similarly, ribozymes can disrupt gene expression by selectively destroying messenger RNA before it is translated into protein. In some embodiments, cells are treated according to the invention using constructs that encode antisense or ribozymes as part of a therapeutic regimen which involves administration of other therapeutics and procedures. Gene constructs encoding antisense molecules and ribozymes use similar vectors as those which are used when protein production is desired except that the coding sequence does not contain a start codon to initiate translation of RNA into protein.

Ribozymes are catalytic RNAs which are capable of self-cleavage or cleavage of another RNA molecule. Several different types of ribozymes, such as hammerhead, hairpin, Tetrahymena group I intron, ahead, and RNase P are known in the art. (S. Edgington, *Biotechnology* 1992 10, 256-262.) Hammerhead ribozymes have a catalytic site which has been mapped to a core of less than 40 nucleotides. Several ribozymes in plant viroids and satellite RNAs share a common secondary structure and certain conserved nucleotides. Although these ribozymes naturally serve as their own substrate, the enzyme domain can be targeted to another RNA substrate through base-pairing with sequences flanking the conserved cleavage site. This ability to custom design ribozymes has allowed them to be used for sequence-specific RNA cleavage (G. Paolella et al., *EMBO* 1992, 1913-1919.) It will therefore be within the scope of one skilled in the art to use different catalytic sequences from various types of ribozymes, such as the hammerhead catalytic sequence and design them in the manner disclosed herein. Ribozymes can be designed against a variety of targets including pathogen nucleotide sequences and oncogenic sequences. Certain preferred embodiments of the invention include sufficient complementarity to specifically target the abl-bcr fusion transcript while maintaining efficiency of the cleavage reaction.

Peptides, polypeptides and protein may be isolated from natural sources, synthesized or produced by recombinant methodology.

Recombinant expression vectors that comprises a nucleotide sequence that encodes proteins of the invention can be produced routinely. As used herein, the term "recombinant expression vector" is meant to refer to a plasmid, phage, viral particle or other vector which, when introduced into an appropriate host, contains the necessary genetic elements to direct expression of a coding sequence. One having ordinary skill in the art can isolate or synthesize a nucleic acid molecule that encodes a protein of the invention and insert it into an expression vector using standard techniques and readily available starting materials. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences. The recombinant expression vectors of the invention are useful for transforming hosts.

Host cells that comprise the recombinant expression vector can be used to produce the protein. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

In some embodiments, for example, one having ordinary skill in the art can, using well known techniques, insert DNA molecules into a commercially available expression vector for use in well known expression systems. For example, the commercially available plasmid pSE420 (Invitrogen, San Diego, Calif.) may be used for production of a CD80AC mutant protein in *E. coli*. The commercially available plasmid pYES2 (Invitrogen, San Diego, Calif.) may, for example, be used for production in *S. cerevisiae* strains of yeast. The commercially available MAXBAC™ complete baculovirus expression system (Invitrogen, San Diego, Calif.) may, for example, be used for production in insect cells. The commercially available plasmid pcDNA I or pcDNA3 (Invitrogen, San Diego, Calif.) may, for example, be used for production in mammalian cells such as Chinese Hamster Ovary cells. One having ordinary skill in the art can use these commercial expression vectors and systems or others to produce proteins of the invention using routine techniques and readily available starting materials. (See e.g., Sambrook et al., *Molecular Cloning a Laboratory Manual*, Second Ed. Cold Spring Harbor Press (1989) which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

The expression vector including the DNA that encodes a protein is used to transform the compatible host which is then cultured and maintained under conditions wherein expression of the foreign DNA takes place. The protein of the invention thus produced is recovered from the culture, either by lysing the cells or from the culture medium as appropriate and known to those in the art. One having ordinary skill in the art can, using well known techniques, isolate the protein of the invention that is produced using such expression systems. The methods of purifying proteins of the invention from natural sources using antibodies which specifically bind to such protein are routine as is the methods of generating such antibodies (See: Harlow, E. and Lane, E., *Antibodies: A Laboratory Manual*, 1988, Cold Spring Harbor Laboratory Press which is incorporated herein by reference). Such antibodies may be used to purifying proteins produced by recombinant DNA methodology or natural sources.

Examples of genetic constructs include coding sequences which encode a protein of the invention and which are operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes proteins of the invention from readily available starting materials. Such gene constructs are useful for the production of proteins of the invention.

In addition to producing proteins of the invention by recombinant techniques, automated peptide synthesizers may also be employed to produce proteins of the invention. Such techniques are well known to those having ordinary skill in the art and are useful if derivatives which have substitutions not provided for in DNA-encoded protein production.

The proteins of the invention may be prepared by any of the following known techniques. Conveniently, the proteins of the invention may be prepared using the solid-phase synthetic technique initially described by Merrifield, in *J Am. Chem. Soc.*, 15:2149-2154 (1963) which is incorporated herein by reference. Other protein synthesis techniques may be found, for example, in M. Bodanszky et al., (1976) *Peptide Synthesis*, John Wiley & Sons, 2d Ed. which is incorporated herein by reference; Kent and Clark-Lewis in *Synthetic Peptides in Biology and Medicine*, p. 295-358, eds. Alitalo, K., et al. Science Publishers, (Amsterdam, 1985) which is incorporated herein by reference; as well as other reference works known to those skilled in the art. A summary of synthesis techniques may be found in J. Stuart and J. D. Young, *Solid Phase Peptide Synthelia*, Pierce Chemical Company, Rockford, Ill. (1984) which is incorporated herein by reference. Synthesis by solution methods may also be used, as described in *The Proteins*, Vol. II, 3d Ed., p. 105-237, Neurath, H. et al., Eds., Academic Press, New York, N.Y. (1976) which is incorporated herein by reference. Appropriate protective groups for use in such syntheses will be found in the above texts, as well as in J. F. W. McOmie, *Protective Groups in Organic Chemistry*, Plenum Press, New York, N.Y. (1973) which is incorporated herein by reference.

In general, these synthetic methods involve the sequential addition of one or more amino acid residues or suitable protected amino acid residues to a growing peptide chain. Normally, either the amino or carboxyl group of the first amino acid residue is protected by a suitable, selectively-removable protecting group. A different, selectively removable protecting group is utilized for amino acids containing a reactive side group, such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to provide the final peptide. The peptide of the invention are preferably devoid of benzylated or methylbenzylated amino acids. Such protecting group moieties may be used in the course of synthesis, but they are removed before the peptides are used. Additional reactions may be necessary, as described elsewhere, to form intramolecular linkages to restrain conformation.

In some embodiments, proteins may be produced in transgenic animals. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes a protein, is operably linked to a mammary cell specific promoter whereby the coding sequence is only expressed in mammary cells and the recombinant protein so expressed is recovered from the animal's milk. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce a desired protein. Preferred animals are goats, and rodents, particularly rats and mice.

In some embodiments, the compound is a nucleic molecule, preferably a DNA molecule. In some embodiments, the nucleic acid molecule is an antisense molecule, which when taken up by the cell, prevents or otherwise inhibits expression of a gene in the cell. In some embodiments, the nucleic acid molecule is a gene construct which contains a coding sequence operably linked to regulatory elements necessary for gene expression of a nucleic acid molecule in the cell.

In addition to a coding sequence, the elements of a gene construct include a promoter, an initiation codon, a stop codon, and a polyadenylation signal. In addition, enhancers are often required for gene expression of the sequence that encodes the protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the individual to whom the gene construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to human and bovine growth hormone polyadenylation signals, SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs of the invention can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In some preferred embodiments related to immunization applications, nucleic acid molecule(s) are delivered which include nucleotide sequences that encode immunogenic proteins, and additionally, genes for proteins which further enhance the immune response against such target proteins. Examples of such genes are those which encode cytokines and lymphokines such as $\alpha$-interferon, gamma-interferon, platelet derived growth factor (PDGF), GC-SF, GM-CSF, TNF, epidermal growth factor (EGF), IL-1, IL-2, IL-4, IL-6, IL-8, IL-10, IL-12 and B7.2.

In order to maximize protein production, regulatory sequences may be selected which are well suited for gene expression in the cells into which the construct is to be administered. Moreover, codons may be selected which are most efficiently transcribed in the cell. One having ordinary skill in the art can produce DNA constructs which are functional in the cells.

In some embodiments, the compound is a DNA molecule. In some embodiments, the compounds is a DNA molecule that is a plasmid. In some embodiments, the compound is a DNA molecule that comprises a nucleotide sequences that encodes a protein operably linked to regulatory elements functional in the cell. In some embodiments, the compound is a DNA molecule that comprises an immunogenic protein operably linked to regulatory elements functional in the cell. In some embodiments, the compound is a DNA molecule that comprises an immunogenic pathogen protein operably linked to regulatory elements functional in the cell. In some embodiments, the compound is a DNA molecule that comprises a non-immunogenic protein operably linked to regulatory elements functional in the cell.

DNA vaccines are described in U.S. Pat. No. 5,93,972, U.S. Pat. No. 5,589,466, PCT/US90/01515, PCT/US93/02338, PCT/US93/048131, and PCT/US94/00899, and the priority applications cited therein each of the patents and published patent applications, which are each incorporated herein by reference. In addition to the delivery protocols described in those applications, alternative methods of delivering DNA are described in U.S. Pat. Nos. 4,945,050 and 5,036,006, which are both incorporated herein by reference.

According to some embodiments, the compound is a protein which includes viral sequences which function to package the compound in the viral particle. In some embodiments, the viral sequences are viral proteins. In some embodiments, the viral sequences are fragments of viral proteins which retain their ability to complex with other viral proteins in the assembly of viral particles. In some embodiments, the particle is an HIV particle and the compound is a fusion protein which includes sequences of the HIV Vpr protein. The fusion protein which includes sequences of the HIV Vpr protein are packaged in the HIV particle.

Non-Cellular Particles

The non-cellular particles according to these aspects of the invention include, but are not limited to, viral particles, protein complexes, liposomes and cationic amphiphile/DNA complexes. According to the invention, such non-cellular particles include a costimulatory molecule ligand or fusion protein which includes a costimulatory molecule ligand portion in order to target the particles to the cells which display costimulatory molecules which bind to the costimulatory molecule ligand or fusion protein displayed by the particle. It has been discovered that in addition to delivering the particles to the cells for localization to cells that display the costimulatory molecule, the particles according to the present invention which are delivered to and localized to cells that display the costimulatory molecule are taken up by the cells.

According to some embodiments of the invention, the particles are viral particles. In preferred embodiments, the particles are non-replicating viral particles. U.S. Pat. No. 5,714, 316, which is incorporated herein by reference, describes the design and production of viral particles which display heterologous protein sequences on the viral particle envelope. The present invention provides an improvement to this technology by providing as the heterologous protein, either a costimulatory molecule ligand or fusion protein which includes a costimulatory molecule ligand portion. In some embodiments, the particles are HIV, HIV, HCV or Papillomavirus particles, preferably non-replicating.

Examples of viral particles according to the invention include non-replicating HIV particles, adenovirus particles, and adenovirus-like particles. Non-replicating viruses are produced using packaging cell lines. Packaging systems are described in each of the following U.S. patents which are incorporated herein by reference: U.S. Pat. Nos. 5,932,467, 5,952,225, 5,932,467, 5,928,913, 5,919,676, 5,912,338, 5,888,767, 5,872,005, 5,866,411, 5,843,723, 5,834,256, 5,753,500, 5,739,018, 5,736,387, 5,723,287, 5,716,832, 5,710,037, 5,693,531, 5,672,510, 5,665,577, 5,622,856, 5,587,308 and 5,585,254.

According to some embodiments, the particles are attenuated vaccines which are improved by providing them with costimulatory ligands to target cells that express costimulatory molecules. Any of the commercially available attenuated vaccines including those currently being investigated such as those undergoing preclinical or clinical premarket testing may be improved by the present invention.

According to some embodiments of the invention, the particles are liposome particles. U.S. Pat. Nos. 4,873,089, 5,227,470 and 5,258,499, which are incorporated herein by reference, describe methods of preparing liposomes that contain proteins displayed on their surfaces in order to target the liposomes to a cell with a cellular protein on its surface that specifically binds to the protein on the surface of the liposome. The present invention provides a specific application of this technology by providing as the receptor ligand, either a costimulatory molecule ligand or fusion protein which includes a costimulatory molecule ligand portion. Liposomes include positive charged, negative charged and neutral liposomes.

According to some embodiments of the invention, 'the particles are cationic amphiphile/DNA complexes. U.S. Pat. Nos. 5,837,533, 5,459,127 and Behr, J. P., et al. (1989) Proc. Natl. Acad. Sci. USA 86:6 82-6986, which are each incorporated herein by reference, describe the design and production of receptor targeted cationic amphiphile/DNA completes in which positively charged lipophilic compounds are provided with receptor ligands. The cationic amphiphilic compounds contain receptor ligand moieties which are displayed on the surface of complexes formed when the cationic amphiphile is mixed with DNA. Such teachings may also be applied to cationic lipid/DNA complexes such as those described in U.S. Pat. Nos. 5,955,365, 5,948,767, 5,945,400, 5,939,401, 5,935,936, 5,932,241, 5,925,628, 5,916,803, 5,910,488, 5,908,635, 5,891,468, 5,885,613, 5,830,430, 5,827,703, 5,783,565 and 5,767,099, which are incorporated herein by reference. In some embodiments, receptor ligand moieties are not linked to any molecule or are linked to neutral lipids which are mixed with the cationic amphiphile and DNA and incorporated into any complexes formed thereby. According to the present invention, cationic amphiphile/DNA are provided with receptor ligands that are costimulatory molecule ligands. Such complexes are targeted to cells that display costimulatory molecules. The complexes localize to and are taken up by the cells.

According to some embodiments of the invention, the particles are protein complexes which comprise two or more protein molecules. The protein complexes comprise a compound to be delivered and a costimulatory ligand.

Cells

The present invention provides methods of delivering compounds to a cells that expresses costimulatory molecules. Typically, cells that express costimulatory molecules are antigen presenting cells. In some embodiments, the method is directed at delivering compounds to a cell that expresses costimulatory molecules that is a dendretic cell. In some embodiments, the method is directed at delivering compounds to a cell that expresses costimulatory molecules that is a macrophage cell.

By delivering immunogens to these cells, immune responses can be generated. By delivering therapeutic proteins which modulate immune responses to these cells, immune responses can be modified. By delivering toxins to these cells, immune responses can be reduced. By delivering growth factors to these cells, immune responses can be enhanced.

Ligands

The costimulatory ligand is a molecule that specifically binds to a costimulatory molecule. In some embodiments, the costimulatory ligand is a protein, preferably an anti-costimulatory molecule antibody, a natural ligand that is specific for the costimulatory molecule or a fusion protein which comprises either an anti-costimulatory molecule antibody, natural ligand or functional fragment thereof.

Anti-costimulatory molecule antibody can be prepared from readily available starting materials using routine techniques. Antibodies against CD80, CD86, CD40, ICOSL, ICAM-1, 41BB, MCSFR, FLT3, CCR-5, CCR-3 and CCR-2 may be used in particles of the invention in order to target the particles to cells expressing CD80, CD86, CD40, ICOSL, ICAM-1, 41BB, MCSFR, FLT3, CCR-5, CCR-3 and CCR-2 respectively.

Alternatively, natural ligands of CD80, CD86, CD40, ICOSL, ICAM-1, 41BB, MCSFR, FT3, CCR-5, CCR-3 and CCR-2 may be provided as costimulatory ligands in order to target the particles to cells expressing CD80, CD86, CD40, ICOSL, ICAM-1, 41BB, MCSFR, FLT3, CCR-5, CCR-3 and CCR-2 respectively. The natural ligands include: CD28 and CTLA-4 which are both natural ligands for CD80; CD28, a natural ligand for CD86; CD40L, the natural ligand for CD40; ICOS, the natural ligand for ICOSL; LFA-3 the natural ligand for ICAM-1; 41BBL, the natural ligand for 41BB; MCSF, the natural ligand for MCSFR; FL3L, the natural ligand for FLT3; MCP3 and RANTES, the natural ligand for CCR-5, CCR-3 and CCR-2. The methods for preparing or otherwise obtaining these proteins are well known.

In some embodiments, the costimulatory ligand is a fusion protein which includes a costimulatory ligand portion. In some embodiments, the costimulatory ligand is portion is an anti-costimulatory molecule antibody. In some embodiments, the costimulatory ligand is portion is a complete natural costimulatory ligand molecule. In some embodiments, the costimulatory ligand portion is a fragment of a natural costimulatory ligand molecule which retains its ability to bind to a costimulatory molecule.

In some embodiments the costimulatory ligand is a fusion protein which comprises amino acid sequences which function in particle assembly or are involved in localizing the fusion protein on the particle. For example, in some embodiments the fusion protein further comprises viral protein sequences which function in particle assembly such that the fusion protein becomes part of a viral particle. In some embodiments, the costimulatory ligand is a fusion protein that includes a costimulatory ligand portion and a viral protein portion. In some embodiments, the viral protein portion is a complete viral protein molecule. In some embodiments, the viral protein portion is a fragment of a viral protein. In some embodiments, the viral protein portion is a fragment of a viral protein that comprise the internal domain and transmembrane regions of a viral protein linked to a functional costimulatory ligand portion. In some embodiments, the fusion protein consists of the portions of the viral protein which are responsible for viral entry into the cell. In some embodiments, the fusion protein consists of the internal domain, transmembrane region and 5-20 amino acids of the external region of a viral protein linked to the extracellular region of a natural ligand of a costimulatory molecule.

In some embodiments, the viral protein portion is derived from a lentivirus such as HIV, from a flavivirus such as yellow fever virus, hepatitis C, JEV, West Nile River Virus or hepatitis E, from a pox virus such as avipox, fowlpox, vaccina, MVA or WR. In some embodiments, the viral protein portion is derived from influenza, rotavirus, cytomegalovirus, rabies virus. In some embodiments, the viral protein portion is selected from the group consisting of HIV gp41, HIV gD, HIV gC, HIV gI, HCV E1, Papillomavirus L1 and Papillomavirus L2. In some embodiments, the viral protein portion is selected from the group consisting of flavivirus E or M protein, poxvirus E or M protein, rotavirus G protein, rabies virus G protein, influenza virus HA protein and CMV GB protein. Importantly, the viral protein portion must contain sufficient viral sequences to be assembled within the viral particle when the particle is assembled. Viral sequences of the fusion protein interact with viral proteins to become included in the viral particle.

In some embodiments, the viral particle contains both a fusion protein and a wild type envelope protein. In some embodiments, the viral particle is free of wild type envelope protein.

In some embodiments, the fusion protein comprises two or more costimulatory ligand portions including two costimulatory ligand portions linked by a linker 15-30 amino acids, preferably about 22 amino acids. Such a fusion protein is particularly useful in preparing targeted liposomes. The duplicate costimulatory ligand portions may proceed N terminal to C terminal, linker, N terminal to C terminal which is particularly useful since it allows for the fusion protein to be prepare by recombinant means. In some embodiments, the formula is N terminal to C terminal, linker, C terminal to N terminal. In some embodiments, the formula is C terminal to N terminal, linker, N terminal to C terminal. In some embodiments, the formula is C terminal to N terminal, linker, C terminal to N terminal.

In some embodiments, the fusion protein comprises one or more costimulatory ligand portions linked to a hydrophobic tail.

In some embodiments, the fusion protein comprises one or more costimulatory ligand portions linked to a polycationic tail, such as a polylysine tail.

In some embodiments, the fusion protein comprises a costimulatory ligand portion linked to a second portion which complexes with a protein to be delivered. In such embodiments, the costimulatory ligand portion complexes to the compound directly.

Methodology and Compositions

Methods of the present invention comprise the step of administering non-cellular particles to tissue of the individual. In some preferred embodiments, the non-cellular particles are administered intramuscularly, intranasally, intraperatoneally, subcutaneously, intradermally, intravenously, by aerosol administration to lung tissue or topically or by lavage to mucosal tissue selected from the group consisting of vaginal, rectal, urethral, buccal and sublingual.

An aspect of the present invention relates to pharmaceutical compositions useful in the methods of the present invention. The pharmaceutical compositions comprise the non-cellular particles which comprise a compound and a costimulatory molecule or fusion protein. The pharmaceutical compositions further comprise a pharmaceutically acceptable carrier or diluent. The term "pharmaceutical" is well known and widely understood by those skilled in the art. As used herein, the terms "pharmaceutical compositions" and "injectable pharmaceutical compositions" are meant to have their ordinary meaning as understood by those skilled in the art. Pharmaceutical compositions are required to meet specific standards regarding sterility, pyrogens, particulate matter as well as isotonicity and pH. For example, injectable pharmaceuticals are sterile and pyrogen free.

In embodiments in which the pharmaceutical compositions according to the present invention comprise non-cellular particles which include nucleic acid molecules as the compound, a sufficient amount of non-cellular particles are administered to introduce about 1 ng to about 10,000 μg of nucleic acid to the tissue. In some preferred embodiments, the pharmaceutical compositions contain about 2000 μg, 3000 μg, 4000 μg or 5000 μg of DNA. In some preferred embodiments, the pharmaceutical compositions contain about 1000 μg of DNA. In some preferred embodiments, the pharmaceutical compositions contain about 10 ng to about 800 μg of DNA. In some preferred embodiments, the pharmaceutical compositions contain about 0.1 to about 500 μg of DNA. In some preferred embodiments, the pharmaceutical compositions contain about 1 to about 350 μg of DNA. In some preferred embodiments, the pharmaceutical compositions contain about 25 to about 250 μg of DNA. In some preferred embodiments, the pharmaceutical compositions contain about 100 μg DNA.

The pharmaceutical compositions according to the present invention are formulated according to the mode of administration to be used. One having ordinary skill in the art can readily formulate a vaccine or non-immunogenic therapeutic that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free. Pharmaceutical compositions according to the invention include delivery components in combination with nucleic acid molecules which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention. Suitable pharmaceutical carriers are described in *Remington's Pharmaceutical Sciences*, A. Osol, a standard reference text in this field, which is incorporated herein by reference.

The pharmaceutical compositions of the present invention may be administered by any means that enables the active agent to reach the agent's site of action in the body of a mammal. The pharmaceutical compositions of the present invention may be administered in a number of ways depending upon whether local or systemic treatment is desired and upon the area to be treated. Administration may be topical (including ophthalmic, vaginal, rectal, intranasal, transdermal), oral or parenteral. Because peptides are subject to being digested when administered orally, oral formulations are formulated to enterically coat the active agent or otherwise protect it from degradation in the stomach (such as prenuetralization). Parenteral administration includes intravenous drip, subcutaneous, intraperitoneal or intramuscular injection, pulmonary administration, e.g., by inhalation or insufflation, or intrathecal or intraventricular administration. In preferred embodiments, parenteral administration, i.e., intravenous, subcutaneous, transdermal, intramuscular, is ordinarily used to optimize absorption. Intravenous administration may be accomplished with the aid of an infusion pump. The pharmaceutical compositions of the present invention may be formulated as an emulsion.

One skilled in the art would readily comprehend the multitude of pharmaceutically acceptable media that may be used in the present invention. Suitable pharmaceutical carriers are described in *Remington's Pharmaceutical Sciences*, A. Osol, a standard reference text in this field, which is incorporated herein by reference. Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for parenteral, intravenous, intrathecal or intraventricular administration may include sterile aqueous solutions which may also contain buffers, diluents and other suitable additives and are preferably sterile and pyrogen free. Pharmaceutical compositions which are suitable for intravenous administration according to the invention are sterile and pyrogen free. For parenteral administration, the peptides of the invention can be, for example, formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution The pharmaceutical compositions according to the present invention may be administered as a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Formulation of therapeutic compositions and their subsequent administration is believed to be within the skill of those in the art. Usually, the dosage of peptide can be about 1 to 3000 milligrams per 50 kilograms of body weight; preferably 10 to 1000 milligrams per 50 kilograms of body weight; more preferably 25 to 800 milligrams per 50 kilograms of body weight. Ordinarily 8 to 800 milligrams are administered to an individual per day in divided doses 1 to 6 times a day or in sustained release form is effective to obtain desired results.

Preferred Components

In some embodiments, the costimulatory ligand is a fusion protein comprising the extracellular portion of CD28 or FLT3 ligand linked to a portion of HIV gp41. The HIV gp41 portion provides for the fusion protein to be packaged in an HIV particle, which is preferably a non-replicating particle. The CD28 extracellular portion targets the viral particle to cells that express CD80 and CD86. The FLT3 ligand portion targets the viral particle to cells that express FLT3. HIV viral particles localized to these cells take up the viral particles. In some embodiments, the viral particles are provided with fusion proteins that include Vpr sequences that provide for assembly into the viral particle. In some embodiments, the compound is a nucleic acid molecules.

In some embodiments, the compound is DNA; in some embodiments, preferably plasmid DNA. In some embodiments the compound is DNA that comprises a nucleotide sequences that encodes a protein operably linked to regulatory elements functional in the cell. In some such embodiments the protein is an immunogenic protein, preferably in some embodiments, an immunogenic pathogen protein. In other such embodiments, the compounds is DNA that comprises a nucleotide sequences that encodes an non-immunogenic protein operably linked to regulatory elements functional in the cell. In some embodiments the compound is DNA that comprises a nucleotide sequences that encodes a protein operably linked to regulatory elements derived from potent expression viral vectors such as AAV, adenovirus or alpha viruses such as SFV. According to this aspect, the DNA construct is provided with the potent expression sequences within a particle that will not cross react to the immune response generated against a potent expression viral vectors. This will allow boosts while taking advantage of the high expression characteristics of the potent expression viral vectors. The potent expression sequences contain the regulatory sequences, such as the ITR sequences in the case of AAV, a gene of interest and may, if the particle is a virus, optionally include a packaging signal so that the nucleic acid molecule gets incorporated into the viral particle.

In some embodiments, the compound is a protein. In some embodiments, the compound is a viral protein. In some embodiments, the compound is a fusion protein that comprises a viral protein portion and a non-viral protein portion.

In some embodiments, the particle is selected from the group consisting of a viral particle, a protein complex, a liposome and a cationic amphiphile/DNA complex. In some embodiments, the particle is a non-replicating viral particle.

According to some aspects of the present invention, methods of introducing compounds into cells are provided which comprise contacting the cells with particles that comprises the compound and a fusion protein. The fusion protein comprises the extracellular region of FLT-3 ligand and the transmembrane and cytoplasmic regions of HIV-1 gp41. The fusion protein provides an effective means to target the cell for delivery of the compound.

According to some aspects of the present invention, particles comprising a FLT-3 ligand and a therapeutic protein or nucleic acid molecule that encodes a therapeutic protein are used to deliver therapeutic proteins to cells. The present invention provides methods of delivering therapeutic proteins to an individual comprising the step of administering to tissue of the individual at a site on said individual's body, a particle that comprises therapeutic protein or a nucleic acid molecule that encodes a therapeutic protein, and FLT-3 ligand. In some embodiments, the therapeutic protein is a non-immunogenic therapeutic protein such as a growth factor or cytokine. In some embodiments, the therapeutic protein is a fusion protein that comprise a viral portion that facilitates packaging the fusion protein in the particle and an non-viral portion such as a transcription factor, growth factor, chemokine or cytokine portion. The protein or DNA encoding the protein are provided as part of/within the particle. In some embodiments, DNA provided as part of/within the particle is plasmid DNA. In some embodiments, the particle is selected from the group consisting of a viral particle, a protein complex, a liposome and a cationic amphiphile/DNA complex. In some embodiments, the particle is a non-replicating viral particle.

Some embodiments of the invention provide methods of immunizing against cancer comprising administering to an individual, a cancer cell comprising a recombinant expression vector that encodes a FLT-3 ligand. Some embodiments of the invention relate to cancer cells that comprising a recombinant expression vector that encodes a FLT-3 ligand.

According to some embodiments of the invention, a particle that comprises a compound and a FLT-3 ligand is provided. In some embodiments, the FLT-3 ligand is a fusion protein comprising the extracellular region of the natural FLT-3 ligand and the transmembrane and cytoplasmic regions of retrovirus envelope protein. In some embodiments, the FLT-3 ligand is a fusion protein comprising the extracellular region of the natural FLT-3 ligand and the transmembrane and cytoplasmic regions of HIV-1 gp41. In some embodiments, the FLT-3 ligand is a fusion protein comprising the extracellular region of the natural FLT-3 ligand and the transmembrane and cytoplasmic regions of Herpes virus gD, gB, gH or gL. In some embodiments, the compound is a nucleic acid or protein. In some embodiments, the compound is DNA. In some embodiments, the compound is plasmid DNA. In some embodiments, the compound is DNA that comprises a nucleotide sequences that encodes a protein operably linked to regulatory elements functional in the cell. In some embodiments, the compound is DNA that comprises a nucleotide sequences that encodes an immunogenic protein operably linked to regulatory elements functional in the cell. In some embodiments, the compound is DNA that comprises a nucleotide sequences that encodes an immunogenic pathogen protein operably linked to regulatory elements functional in the cell. In some embodiments, the compound is DNA that comprises a nucleotide sequences that encodes an non-immunogenic protein operably linked to regulatory elements functional in the cell. In some embodiments, the compound is a protein. In some embodiment, the compound is a fusion protein that comprises a viral portion that facilitates packaging the fusion protein in the particle and an non-viral portion such as a transcription factor, growth factor, chemokine or cytokine portion. In some embodiments, the viral protein portion is the HIV Vpr protein that binds to Gag resulting in Vpr protein being included in the HIV particle. According to such embodiments, the Vpr protein portion facilitates the inclusion of the fusion protein in the particle. In some embodiments, the particle is selected from the group consisting of a viral particle, a protein complex, a liposome and a cationic amphiphile/DNA complex. In some embodiments, the particle is a non-replicating viral particle. In some embodiments, the particle is a non-replicating HIV or Herpes viral particle.

Transcription factors or portions thereof included as therapeutic proteins or as part of fusion proteins drive and/or modulate gene expression in cells infected by the particles. T-bet is an example of transcription factors which shuts down Th2 responses and promotes Th1 responses. Such an example would be useful in a vaccine. Gata is an example of transcription factors which shut down Th1 responses and promotes Th2 responses. Such an example would be useful in a treatment of autoimmune disease.

Cytokines or portions thereof included as therapeutic proteins or as part of fusion proteins, drive/modulate immune responses as do chemokines or portions thereof included as therapeutic proteins or as part of fusion proteins. An example of a cytokine is IL-15. An example of a chemokine is RANTES.

Therapeutic and fusion proteins may include transport proteins or fragments thereof and processing proteins of fragments thereof. An example of a transport protein is p70. An example of a processing protein is Tap.

In the case of HIV derived particles which packages Vpr protein and fusion proteins which contain Vpr portions, the particles can contain as many as 2400 copies of the fusion protein. The Vpr portion is inactive, it does not contain sequences which induce cell cycle arrest and apoptosis.

The fusion protein may include a protease cleavage site between the two portions. An example of such a cleavage site is the cleavage site recognized by the HIV protease. In addition to HIV-derived particles, the invention is envisioned to include particles and chimerics based upon other lentiviruses and lentivirus proteins. The invention also pertains to the use of free vpr fusions to be delivered as drugs as well.

A further aspect of the invention relates to methods of immunizing individuals. Such comprise the steps of administering to tissue of the individual at a site on the individual's body, a DNA molecule that comprises a nucleotide sequence that encodes an immunogenic protein operably linked to regulatory elements. Subsequently, a particle that comprises an immunogenic protein is administered to the individual. In some embodiments, the particle may further comprises a compound. In some embodiments, the compound may be a nucleic acid molecule. In some embodiments, the compound is DNA. In some embodiments, the compound is plasmid DNA. In some embodiments, the compound is DNA that comprises a nucleotide sequences that encodes an immunogenic protein operably linked to regulatory elements functional in the cell. In some embodiments, the compound is DNA that comprises a nucleotide sequences that encodes an immunogenic pathogen protein operably linked to regulatory elements functional in the cell. In some embodiments, the compound is DNA that comprises a nucleotide sequences that encodes an non-immunogenic protein operably linked to regulatory elements functional in the cell. In some embodiments, the particle is a viral particle. In some embodiments, the particle is a non-replicating viral particle. In some embodiments, the particle is a protein complex.

According to some embodiments, the compounds is a protein which includes viral sequences which function to package the compound in the viral particle. In some embodiments, the viral sequences are viral proteins. In some embodiments, the viral sequences are fragments of viral proteins which retain their ability to complex with other viral proteins in the assembly of viral particles. In some embodiments, the particle is an HIV particle and the compound is a fusion protein which includes sequences of the HIV Vpr protein. The fusion protein which includes sequences of the HIV Vpr protein are packaged in the HIV particle. In some embodiment, the compound is a fusion protein that comprises a viral portion that facilitates packaging the fusion protein in the particle and an non-viral portion such as a transcription factor, growth factor, chemokine or cytokine portion. In some embodiments, the viral protein portion is the portion of HIV Vpr protein that binds to Gag resulting in Vpr protein being included in the HIV particle. According to such embodiments, the Vpr protein portion facilitates the inclusion of the fusion protein in the particle.

Example 3

The present invention relates to compositions useful for delivering fusion proteins into specifically targeted cells. The fusion protein comprises a biologically active portion and a Vpr fragment which binds to HIV viral proteins assembled as part of the viral particle. In some embodiments, the particle additionally contains cell-type specific coat protein to deliver the particle specific to cells that the coat protein binds to. The present invention relates to the fusion proteins, to the particles, to the pharmaceutical compositions that comprise the particles and pharmaceutically acceptable carriers, to the nucleic acid molecules that encode the components, to the expression vectors and host cells that contain the nucleic acid molecules and to the methods of producing and using the compositions.

To prepare a fusion drug delivery particle of the invention, the envelope protein (Env) of a retrovirus is chosen based upon the cell type such a retrovirus infects. Cell specific envelope proteins are well known. A chimeric gene is designed which includes the portion of the Vpr protein that is required for Vpr to be incorporated into the viral particle together with a biological active protein which retains its activity when linked to the portion of vpr. Cells are co-transfected with a nucleic acid molecule that encodes the desired env, the chimeric gene that encodes the fusion protein, a nucleic acid molecule that encodes p24 or a nucleic acid molecule that encodes the full length gag precursor plus the HIV protease. Expression of these sequences will result in the proteins thus encoded being produced and assembly of the drug delivery particle. Noncoding RNA may also be provided for safety since the assembling particle will package RNA.

The particles may be those such as described in Example 2 which comprise the Vpr fusion protein, particles essentially as described in Example 2 which comprise the Vpr fusion protein but which do not contain fusion proteins which have co-stimulatory molecule ligands, particles which are produced by packaging cell lines that produce HIV-derived particles as described in the packaging systems incorporated above which including the chimeric gene that encodes the Vpr fusion protein, particles which are produced by packaging cell lines that contain heterologous Env proteins or fusion Env proteins as described in U.S. Pat. No. 5,714,316.

Biologically active proteins which can be used in fusion proteins include transcription factors, growth factors, cytokines, chemokines, transport proteins and processing proteins.

Example 4

Recombinant Cell Based Cancer Vaccines

Another aspect of the present invention relates to the use of recombinant cancer cells as cancer vaccines. The use of recombinant cancer cells as cancer vaccines is described in U.S. Pat. No. 5,935,569, which is incorporated by references. According to this aspect of the invention, the recombinant gene expressed by the cancer cell is a Flt-3 ligand. The cancer vaccine is an autologous cancer cell transfected with an expression vector that comprises a sequence encoding a Flt-3 ligand. The cancer cells expressing the Flt-3 ligand are targeted to cells that express Flt-3 molecules and the immune response against the cancer cells in enhanced. In preferred embodiments, the recombinant expression vector that comprises a sequence encoding a Flt-3 ligand is transfected into cancer cells ex vivo and the transfected cells are then restored to the patient.

In some embodiments, the transfected cancer cell is further provided with an expression vector that includes a nucleotide sequence that encodes a death domain receptor or death domain signal or a toxin. Death domain receptors include, but are not limited to; Apo-1 (Oehm et al., J. Biol. Chem., 1992, 267(15), 10709-15; Accession Number X63717); Fas (Itoh et al., Cell, 1991, 66(2), 233-43; Accession Number M67454); TNFR-1 (Nophar et al., EMBO J., 1990, 9(10), 3269-78; Accession Number M67454); p55 (Loetscher et al., Cell, 1990, 61, 351-359; Accession Numbers M58286, M33480); WSL-1 (Kitson et al., Nature, 1996, 384(6607), 372-5; Accession: Number Y09392); DR3 (Chinnaiyan et al., Science, 1996, 274 (5829), 990-2; Accession Number U72763); TRAMP (Bodmer et al., Immunity, 1997, 6(1), 79-88; Accession Number U75381); Apo-3 (Marsters et al., Curr. Biol., 1996, 6(12), 1669-76; Accession Number U74611); AIR (Degli-Esposti et al., direct submission, Accession Number U78029); LARD (Screaton et al., Proc. Natl. Acad. Sci. USA, 1997, 94(9), 4615-19; Accession Number U94512); NGRF (Johnson et al., Cell, 1986, 47(4), 545-554; Accession Number M14764); DR4 (Pan et al., Science, 1997, 276(5309), 111-113; Accession Number U90875); DR5 (Sheridan et al., Science, 1997, 277(5327), 818-821; Accession Number AF012535); KILLER (Wu et al., Nature Genetics, in press; TRAIL R2 (MacFarlane et al, J. Biol. Chem., 1997, in press; Accession Number AF020501); TRICK2 (Screaton et al., Curr. Biol., 1997, in press; Accession Number AF018657); DR6 (Pan et al., unpublished; Accession Number AF068868). Death signals, i.e. proteins that interact with the death domain receptors include, but are not limited to; FADD (Chinnaiyan et al., Cell, 1995, 81(4), 505 12; Accession Number U24231); FAP-1 (Sato et al., Science, 1995, 268 (5209), 411-15; Accession Number L34583); TRADD (Hsu et al., Cell, 1995, 81(4), 495 504; Accession Number L41690); RIP (Stanger et al., Cell, 1995, 81(4), 513-23; Accession Number U25994); and FLICE (Muzio et al., Cell, 1996, 85(6); 817-27; Accession Number U58143); RAIDD (Lennon et al., Genomics, 1996, 33(1), 151-2; Accession Number U79115). Death signals also include ligands that bind death domain receptors and initiate apoptosis include, but are not limited to; FAS-L (Alderson et al., J. Exp. Med., 1995, 181(1), 71-7; Accession Number U08137), and TNF, and mediators that interact with death domain receptors include, but are not limited to; FADD (Chinnaiyan et al., Cell, 1995, 81(4), 505-12; Accession Number U24231); MORT1 (Boldin et al., J. Biol. Chem., 1995, 270(14), 7795-8; Accession Number X84709); CRADD (Ahmad et al., Cancer Res., 1997, 57(4), 615-9; Accession Number U84388); and MyD88 (Bonnert et al, FEBS Lett., 1997, 402(1), 81-4; Accession Number U84408). Toxins include proteins which kill cells. Toxins include but are not limited to insect and snake venoms, bacterial endotoxins such as Psuedomoneus endotoxin, double chain ribosome inactivating proteins such as ricin including single chain toxin, and gelonin.

TABLE 1

Picornavirus Family

| | |
|---|---|
| Genera: | Rhinoviruses: (Medical) responsible for ~50% cases of the common cold.<br>Enteroviruses: (Medical) includes polioviruses, Coxsackieviruses, echoviruses, and human enteroviruses such as hepatitis A virus.<br>Apthoviruses: (Veterinary) these are the foot and mouth disease viruses. |
| Target antigens: | VP1, VP2, VP3, VP4, VPG |

Calcivirus Family

| | |
|---|---|
| Genera: | Norwalk Group of Viruses: (Medical) these viruses are an important causative agent of epidemic gastroenteritis. |

Togavirus Family

| | |
|---|---|
| Genera: | Alphaviruses: (Medical and Veterinary) examples include Sindbis viruses, RossRiver virus and Eastern & Western Equine encephalitis.<br>Rubivirus: (Medical) Rubella virus. |
| Flaviviridue Family | Examples include: (Medical) dengue, yellow fever, Japanese encephalitis, St. Louis encephalitis and tick borne encephalitis viruses. |
| Hepatitis C Virus: | (Medical) these viruses are not placed in a family yet but are believed to be either a togavirus or a flavivirus. Most similarity is with togavirus family. |
| Coronavirus Family: | (Medical and Veterinary)<br>Infectious bronchitis virus (poultry)<br>Porcine transmissible gastroenteric virus (pig)<br>Porcine hemagglutinating encephalomyelitis virus (pig)<br>Feline infectious peritonitis virus (cats)<br>Feline enteric coronavirus (cat)<br>Canine coronavirus (dog)<br>The human respiratory coronaviruses cause ~40 cases of common cold. EX. 224E, OC43<br>Note - coronaviruses may cause non-A, B or C hepatitis |
| Target antigens: | E1 - also called M or matrix protein<br>E2 - also called S or Spike protein<br>E3 - also called HE or hemagglutin-elterose glycoprotein (not present in all coronaviruses)<br>N - nucleocapsid |

Rhabdovirus Family

| | |
|---|---|
| Genera: | Vesiculovirus: Vesicular Stomatitis Virus<br>Lyssavirus: (medical and veterinary) rabies |
| Target antigens: | G protein<br>N protein |
| Filoviridue Family: | (Medical)<br>Hemorrhagic fever viruses such as Marburg and Ebola virus |

Paramyxovirus Family:

| | |
|---|---|
| Genera: | Parainfluenza Virus Type 1<br>Parainfluenza Virus Type 3<br>Bovine Parainfluenza Virus Type 3<br>Rubulavirus: (Medical and Veterinary)<br>Mumps virus, Parainfluenza Virus Type 2, Parainfluenza Virus Type 4, NewCastle disease virus (important pathogen in chickens)<br>Morbillivirus: (Medical and Veterinary)<br>Measles, canine distemper<br>Pneumonvirus: (Medical and Veterinary)<br>Respiratory syncytial virus |
| Orthomyxovirus Family | (Medical)<br>The Influenza virus |

Bunyavirus Family

| | |
|---|---|
| Genera: | Bunyavirus: (Medical) California encephalitis, La Crosse<br>Phlebovirus: (Medical) Rift Valley Fever<br>Hantavirus: Puremala is a hemahagin fever virus<br>Nairovirus (Veterinary) Nairobi sheep disease<br>Also many unassigned bungaviruses |
| Arenavirus Family | (Medical)<br>LCM, Lassa fever virus |

Reovirus Family

| | |
|---|---|
| Genera: | Reovirus: a possible human pathogen<br>Rotavirus: acute gastroenteritis in children<br>Orbiviruses: (Medical and Veterinary)<br>Cultivirus: Colorado Tick fever, Lebombo (humans) equine encephalosis, blue tongue |

TABLE 1-continued

| Retrovirus Family | |
|---|---|
| Sub-Family: | Oncorivirinal: (Veterinary) (Medical) feline leukemia virus, HTLVI and HTLVII |
| | Lentivirinal: (Medical and Veterinary) HIV, feline immunodeficiency virus, equine infections, anemia virus |
| | Spumavirinal |
| Papovavirus Family | |
| Sub-Family: | Polyomaviruses: (Medical) BKU and JCU viruses |
| Sub-Family: | Papillomavirus: (Medical) many viral types associated with cancers or malignant progression of papilloma |
| Adenovirus | (Medical) |
| | EX AD7, ARD., O.B. - cause respiratory disease - some adenoviruses such as 275 cause enteritis |
| Parvovirus Family | (Veterinary) |
| | Feline parvovirus: causes feline enteritis |
| | Feline panleucopeniavirus |
| | Canine parvovirus |
| | Porcine parvovirus |
| Herpesvirus Family | |
| Sub-Family: | alphaherpesviridue |
| Genera: | Simplexvirus (Medical) |
| | HSVI, HSVII |
| | Varicellovirus: (Medical - Veterinary) pseudorabies - varicella zoster |
| Sub-Family- | betaherpesviridue |
| Genera: | Cytomegalovirus (Medical) |
| | HCMV |
| | Muromegalovirus |
| Sub-Family: | Gammaherpesviridue |
| Genera: | Lymphocryptovirus (Medical) |
| | EBV - (Burkitts lympho) |
| | Rhadinovirus |
| Poxvirus Family | |
| Sub-Family: | Chordopoxviridue (Medical - Veterinary) |
| Genera: | Orthopoxvirus |
| | Variola (Smallpox) |
| | Vaccinia (Cowpox) |
| | Parapoxivirus - Veterinary |
| | Auipoxvirus - Veterinary |
| | Capripoxvirus |
| | Leporipoxvirus |
| | Suipoxvirus |
| Sub-Family: | Entemopoxviridue |
| Hepadnavirus Family: | Hepatitis B virus |
| Unclassified: | Hepatitis delta virus |

TABLE 2

Bacterial pathogens

Pathogenic gram-positive cocci include: pneumococcal; staphylococcal; and streptococcal. Pathogenic gram-negative cocci include: meningococcal; and gonococcal.
Pathogenic enteric gram-negative bacilli include: enterobacteriaceae; *pseudomonas*, acinetobacteria and *eikenella*; melioidosis; *salmonella*; shigellosis; *hemophilus*; *moraxella*; chancroid; brucellosis; tularemia; *yersinia* (*pasteurella*); *streptobacillus moniliformis* and *spirillum*; *listeria monocytogenes*; *erysipelothrix rhusiopathiae*; diphtheria; cholera; anthrax; donovanosis (granuloma inguinale); and bartonellosis.
Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphilis; and leptospirosis.
Other infections caused by higher pathogen bacteria and pathogenic fungi include: actinomycosis; nocardiosis; cryptococcosis, blastomycosis, histoplasmosis and coccidioidomycosis; candidiasis; aspergillosis, and mucormycosis; sporotrichosis; paracoccidiodomycosis, petriellidiosis, torulopsosis, mycetoma and chromomycosis; and dermatophytosis.
Rickettsial infections include rickettsial and rickettsioses.
Examples of mycoplasma and chlamydial infections include: *mycoplasma pneumoniae*; lymphogranuloma venereum; psittacosis; and perinatal chlamydial infections.

TABLE 2-continued

Pathogenic eukaryotes

Pathogenic protozoans and helminths and infections thereby include: amebiasis; malaria; leishmaniasis; trypanosomiasis; toxoplasmosis; *pneumocystis* carinii; babesiosis; giardiasis; trichinosis; filariasis; schistosomiasis; nematodes; trematodes or flukes; and cestode (tapeworm) infections.

The invention claimed is:

1. A non-cellular particle that comprises
 a) a fusion protein comprising
  i) Flt-3 ligand or a FLT-3 binding fragment thereof and
  ii) transmembrane and cytoplasmic regions of HIV-1 gp41 and
 b) a nucleic acid molecule.

2. The particle of claim 1, wherein said nucleic acid molecule is DNA.

3. The particle of claim 1 wherein the particle is a viral particle, a protein complex, a liposome or a cationic amphiphile/DNA complex.

4. The particle of claim 3 wherein the particle is a viral particle.

5. The particle of claim 2 wherein the particle is a viral particle.

6. A method of introducing a nucleic acid molecule into a cell that expresses Flt3 molecules, said method comprising contacting the cell with a non-cellular particle of claim 1.

7. The method of claim 6 wherein the compound is DNA.

8. The method of claim 6 wherein the particle is a viral particle, a protein complex, a liposome or a cationic amphiphile/DNA complex.

9. The method of claim 8 wherein the particle is a viral particle.

10. The method of claim 7 wherein the particle is a viral particle.

* * * * *